(12) United States Patent
Chien et al.

(10) Patent No.: US 9,804,109 B2
(45) Date of Patent: Oct. 31, 2017

(54) SYSTEM AND METHOD FOR CHEMICAL AND/OR BIOLOGICAL DETECTION

(75) Inventors: Poliang Chien, Rancho Palos Verdes, CA (US); Dheeraj Jain, Tustin, CA (US); Kelley Lowery, Mission Viejo, CA (US); Ryan Hur, Irvine, CA (US)

(73) Assignee: Design West Technologies, Inc., Tustin, CA (US)

( * ) Notice: Subject to any disclaimer, the term of this patent is extended or adjusted under 35 U.S.C. 154(b) by 514 days.

(21) Appl. No.: 13/468,945

(22) Filed: May 10, 2012

(65) Prior Publication Data

US 2014/0004618 A1   Jan. 2, 2014

(51) Int. Cl.
| | |
|---|---|
| *G01N 27/00* | (2006.01) |
| *G01N 27/12* | (2006.01) |
| *G01N 33/00* | (2006.01) |
| *G01N 1/22* | (2006.01) |
| *G01N 1/24* | (2006.01) |

(52) U.S. Cl.
CPC .......... *G01N 27/00* (2013.01); *G01N 1/2273* (2013.01); *G01N 1/24* (2013.01); *G01N 27/127* (2013.01); *G01N 33/0057* (2013.01)

(58) Field of Classification Search
CPC ...... G01N 27/126; G01N 27/12; G01N 27/60; G01N 33/0031; G01N 27/002; G01N 27/3271; G01N 33/5438; G01N 27/414; G01N 33/54373; G01N 27/00; B01J 19/0046; B01J 2219/00722; B01J 2219/00659; B01L 2300/0816; C40B 40/06; B82Y 15/00

USPC .............................. 436/151; 422/68.1, 82.01
See application file for complete search history.

(56) References Cited

U.S. PATENT DOCUMENTS

| | | | | |
|---|---|---|---|---|
| 4,705,669 | A  * | 11/1987 | Tsuji et al. ...................... | 422/93 |
| 5,104,553 | A  * | 4/1992 | Lorenz et al. ................. | 210/741 |
| 6,245,296 | B1 * | 6/2001 | Ligler .................... | G01N 33/53 422/402 |
| 6,837,095 | B2 * | 1/2005 | Sunshine et al. .............. | 73/23.2 |
| 8,000,903 | B1 * | 8/2011 | Li ......................... | G01N 27/127 422/83 |
| 2007/0202012 | A1 * | 8/2007 | Steichen ............ | G01N 33/0031 422/98 |

(Continued)

OTHER PUBLICATIONS

Nanotube Molecular Wires as Chemical Sensors Jing Kong, Nathan R. Franklin, Chongwu Zhou, Michael G. Chapline, Shu Peng, Kyeongjai Cho, Hongjie Dai Science vol. 287, pp. 622-625, Jan. 28, 2000.*

*Primary Examiner* — Krishnan S Menon
*Assistant Examiner* — Dwan A Gerido
(74) *Attorney, Agent, or Firm* — Inskeep IP Group, Inc.

(57) ABSTRACT

A method and system for detecting the presence of chemical and/or biological agents are disclosed. An additive, which may comprise a reactant and/or a catalyst selected for its capacity to react with, or to force a reaction involving a target chemical and/or biological agent, may be introduced into a sample of an ambient environment to be monitored. The additive may then react with the target agent, or, as a catalyst, may drive a reaction with the target agent, resulting in a reaction product that may be detected by one or more sensors or sensor arrays. The method and system may incorporate a plurality of sensor types in order to enhance the specificity of the method and system.

12 Claims, 26 Drawing Sheets

(56) References Cited

U.S. PATENT DOCUMENTS

2011/0226619 A1* 9/2011 Eckhardt .............. G01N 27/401
                                                                                               204/417

* cited by examiner

SYSTEM AND METHOD FOR CHEMICAL AND/OR BIOLOGICAL DETECTION

FIELD OF THE INVENTION

The present invention relates generally to the field of chemical and/or biological agent detection. More particularly, the present invention provides a useful and novel system and method for detecting target chemical or biological agents wherein an additive, which may be a reactant, selective absorber, and/or catalyst, is introduced into a sample to produce a measurable reaction product in the presence of a target chemical and/or biological agent.

BACKGROUND OF THE INVENTION

Chemical and/or biological agent detection finds a wide variety of applications, such as detection of explosives and toxic chemicals in law enforcement and anti-terrorist efforts, environmental and agricultural contamination monitoring, medical diagnosis, and detection of chemical warfare agents.

The usefulness of carbon nanotube (CNT) structures in the field of chemical detection has been demonstrated. CNTs are molecular-scale 'wires'. CNTs-based sensors are capable of detecting small concentrations of gas molecules. The conductance of CNTs can be substantially increased or decreased by exposure to certain gas molecules. Reference: *Nanotube Molecular Wires as Chemical Sensors*; Jing King, et al.; Science Magazine; Vol. 287; Jan. 28, 2000. Therefore, by measuring the change in an electrical property of a CNT sensors, such as resistance, capacitance, voltage or conductance, it is possible to detect the presence of a chemical that drives a change in that electrical property, and to identify the present chemical by comparing the magnitude, rate and direction of change of the electrical property to those changes known to result from exposure of the sensor to a particular chemical or biological agent.

CNT sensor technology is attractive because it may be implemented in a simple, compact, and relatively inexpensive apparatus. Further, CNT sensor technology is functional at ambient temperatures and provides rapid response times and reproducible responses.

There exist limitations and disadvantages associated with conventional methods and systems for application of CNT sensor technology to the detection of chemical and/or biological agents. These limitations fall generally into the categories of sensitivity, or the capability to detect a particular target agent, specificity, or the capability to specifically distinguish the agent that is detected, and false alerts.

A significant limitation in the utility and application of CNT sensor technology is limited sensitivity, or the ability of CNTs to detect certain agents or concentration levels of agents of interest. For example, carbon nanotube-based sensor systems do not have the capacity to detect low, yet dangerous concentrations of cyanogen chloride (CK), a key agent of interest in the field of chemical warfare detection.

In terms of specificity, a particular sensor may respond to a variety of chemical and/or biological agents. Adhering to the exemplar of CNT sensors applied to CK detection, there exist a plurality of chemicals that may alter the electrical properties of a CNT sensor, thereby providing an alert as to the presence of a chemical. Some of these chemicals may alter the electrical properties of the CNT sensor in the same direction, magnitude and/or rate as does CK. Therefore, it is possible to receive a false alert wherein the system may indicate the presence of CK when, in fact, CK is not present. Even a change in the relative humidity of the ambient environment in which a detection method is conducted may cause a change in the electrical properties of a CNT sensor.

What is needed is a system and method that may be implemented in a simple, compact, and relatively inexpensive apparatus that is functional at ambient temperatures, and provides rapid response times and reproducible responses. Further, the needed system and method must be capable of detecting chemical and/or biological agents of interest, differentiating the presence of the specific agent of interest from the presence of other present agents and, thereby, eliminating false alerts.

SUMMARY OF THE INVENTION

In view of the foregoing limitations and disadvantages inherent to the conventional systems and methods in the related art, the present invention provides a novel system [hereinafter "additive-enhanced detection system"] for detecting the presence of a chemical and/or biological agent, and a method of using the system [hereinafter "additive-enhanced detection"].

A principal object of the present invention is to enable detection of target chemical and/or biological agents, or concentrations of such target chemical and/or biological agents, that may not otherwise practically be detectable by a particular sensor type.

In one aspect, the present invention incorporates an additive, which may comprise a reactant, selective absorber, and/or a catalyst selected for its capacity to react with or to force a reaction involving the target agent, into the detection method and system. The additive may be mixed with a sample of an ambient environment. The additive may then react with the detection target agent, or, as a catalyst/selective absorber, may drive a reaction with the detection target agent, resulting in a reaction product that may be detected by one or more sensors or sensor arrays.

Another object of the present invention is to dampen the moisture content fluctuations in an environment sample where required either 1) to enable a chemical reaction or 2) to correlate output of a chemical and/or detection system and method to pre-determined predicted detection response data.

In another aspect, the present invention incorporates a water vapor additive reservoir comprising a reservoir containing either liquid water or an air supply with a particular moisture content. The water vapor additive reservoir further comprises permeable tubing designed to enable the liquid water or humid air supply to permeate into or out of an environment sample. As an unconditioned environment sample passes through the moisture buffer, the moisture content of the environmental sample is regulated and/or maintained by means of moisture passing through the permeable tubing.

A further object of the present invention is to enhance the specificity, or the capability to distinguish the agent that is detected, of a detection system and method. An advantage attendant to an increase in specificity is the reduction of sources of false alerts.

In a further aspect, the present invention incorporates two or more multi-sensor arrays, each array incorporating a plurality of sensor types. Each of the sensor types may be selected to provide or contribute to a distinguishing detection signature for various chemical and/or biological agents of interest when used in combination with the other sensor type or types.

Other objects, aspects and advantages of the present invention will become readily apparent to those with skill in the art from the following figures, descriptions and claims.

As will be appreciated by those with skill in the art, the method of the present invention may be implemented in a plurality of equivalent steps, and the system may be implemented in a plurality of equivalent embodiments. Such alternative method steps and system embodiments, and their attendant objects, aspects and advantages, are within the scope of the present invention and, therefore, the examples set forth herein shall not be limiting. Further, although in the interest of continuity of the disclosure this specification will focus on exemplary embodiments that may find their primary application in chemical warfare agent detection, any useful application within any field of use is within the contemplation of the present invention.

BRIEF DESCRIPTION OF THE DRAWINGS

The nature of this invention, as well as all its objects, aspects and advantages, will become readily apparent and understood upon reference to the following detailed description when considered in conjunction with the accompanying drawings, in which like reference numerals designate like parts throughout the figures thereof, and wherein.

DETAILED DESCRIPTION OF THE INVENTION

The following description is provided to enable a person skilled in the relevant art to make and use the invention, and sets forth the best modes contemplated by the inventor of carrying out the invention. The present invention shall not be limited to the examples disclosed. Rather, the scope of the invention shall be as broad as the claims will allow.

Various inventive features are described below that can each be used independently of one another or in combination with other features. However, any single inventive feature may not address any of the disadvantages discussed above, or might only address one of the disadvantages discussed above. Further, one or more of the disadvantages discussed above may not be fully addressed by any of the features described below.

Figure 1:
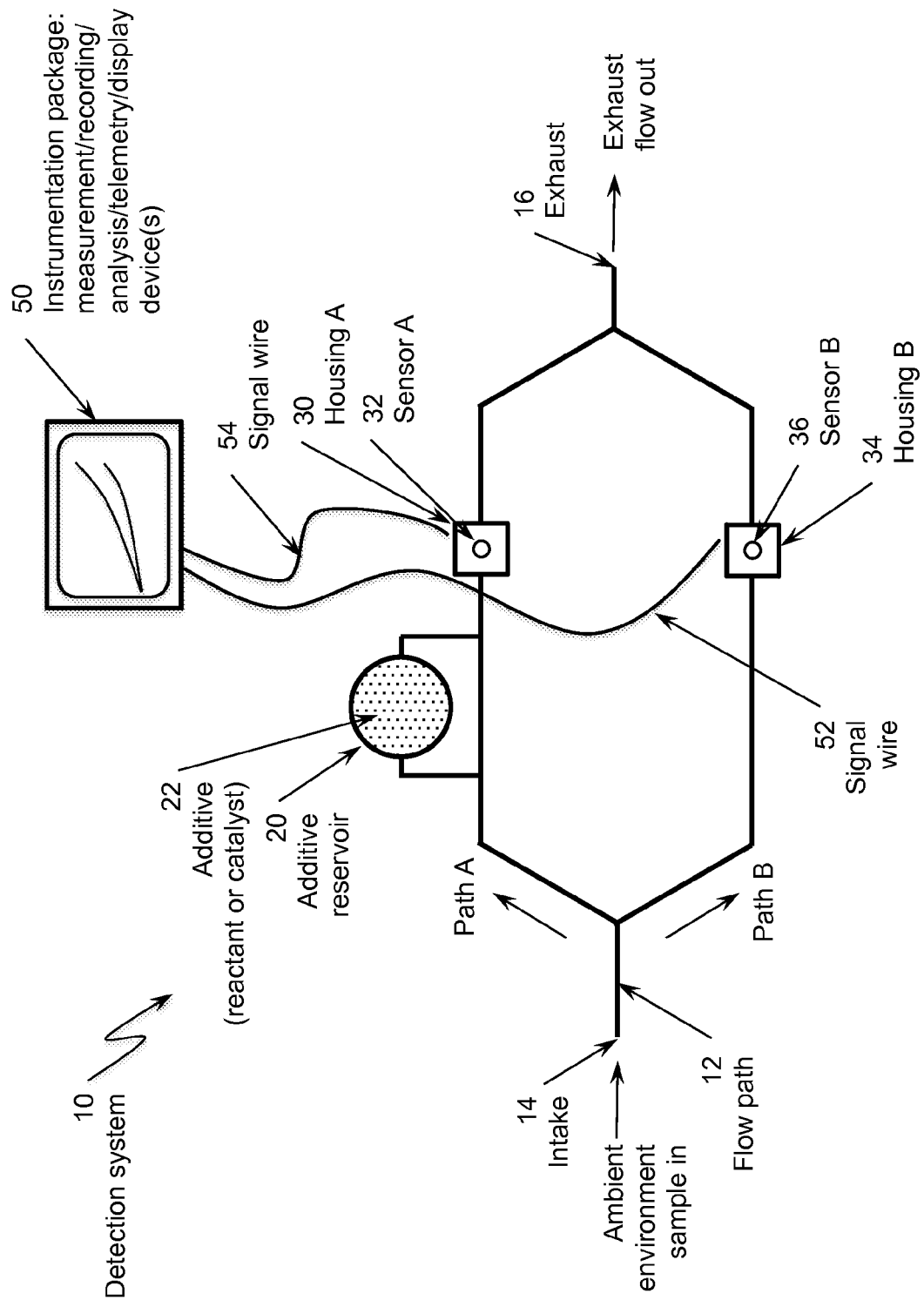
FIG. 1 presents a block diagram of a system for detecting chemical and/or biological agents, according to one exemplary embodiment of the present invention.

Referring now to the drawings, FIG. 1 presents a block diagram of an additive-enhanced detection system 10 according to one embodiment of the present invention, comprising a flow path 12 that may be designed and configured to direct the flow of samples of an ambient environment into which the additive-enhanced detection system 10 is placed. The flow path 12 may have an intake 14 designed to enable a sample of the ambient environment to enter the flow path 12, and an exhaust 16 designed to enable the ambient environment sample to exit the flow path 12.

Downstream of the intake 14, the flow path 12 may be separated into Path A and Path B, as illustrated in FIG. 1. A housing B 34 may be integrated into, and in fluid communication with Path B. A sensor B 36 may be contained within housing B 34 such that sensor B 36 may be exposed to the ambient environment sample as the sample flows through Path B. Sensor B 36 may be electrically connected, by means of an electrically conductive signal wire 52, to an instrumentation package 50 that may be designed and configured to measure, record, analyze, communicate and/or display an electrical, mechanical, chemical, electrochemical and/or electromechanical property of sensor B 36 over time.

A housing A 30 may be integrated into, and in fluid communication with Path A. A sensor A 32 may be contained within housing A 30 such that the sensor A 32 may be exposed to the ambient environment sample as the sample flows through Path A. Sensor A 32 may be connected, by means of an electrically conductive signal wire 54 to an instrumentation package 50 that may be designed and configured to measure, record, analyze, communicate and/or display an electrical, mechanical, chemical, electrochemical and/or electromechanical property of sensor B 32 over time.

An additive reservoir 20 may be integrated into, and in fluid communication with Path A upstream of sensor A 32. The additive reservoir 20 may contain an additive 22, and may be designed to introduce the additive 22 into Path A, thereby causing the additive to be mixed with the ambient environment sample as the sample flows through Path A. The additive 22 may be a reactant, selective absorber, and/or a catalyst selected for its capacity to cause and/or participate in a chemical reaction, the reaction product of which may be detected by the sensor A 32, when mixed with the ambient environment sample.

The additive 22 may be in solid, liquid or vapor form. The additive reservoir 20 may perform the mixing function by, any practical or useful means, including but not limited to a liquid bath, chemical jet, positive pressure pump, heat evaporation, capillary action, siphon suction, or Bernoulli's principle. Per Bernoulli's principle, the additive is delivered to the sensor or sensor array without use of additional energy. The amount of additive delivered to the sensor or sensor array is controlled by saturated vapor pressure of the additive and the flow rate of the sample of an ambient environment.

An instrumentation package 50 may include one or more devices for measuring changes in an electrical, mechanical, chemical, electrochemical and/or electromechanical property (such as current, capacity, or resistance across a sensor), recording measured and/or calculated data, analyzing measured and/or calculated data, telemetry of measured and/or calculated data to a remote user, and displaying measured and/or calculated data. The one or more devices may be packaged individually or integrated into one or more subsystems.

Non-limiting examples of devices that may be incorporated into the instrumentation package 50 include the following. A device for measuring changes in an electrical property may be an ohmmeter, an amp meter, a Faraday plate or a photodiode. A device for recording measured and/or calculated data may be a machine-readable memory. A device for analyzing measured and/or calculated data may be a computer processor or microprocessor in combination with logic, commands and algorithms stored in on a machine-readable medium. A device for telemetry of measured and/or calculated data may be a transmitter or a transceiver. A device for displaying measured and/or calculated data may include a video screen, a printing device, a photographic device, or any useful medium for communicating system output. The instrumentation package 50 may incorporate a means of providing power to the various devices, such as a battery and/or a power generation means such as a solar power generation device.

The system and method of the present invention may be adapted to application in a variety of fields, such as chemical warfare and industrial chemical detection, and to the detection of a wide variety of target chemical and/or biological agents, employing a variety of sensor types.

As will be appreciated by those with skill in the relevant art, the system and method may be modified depending upon the specific application and/or target agent. The various sensor types may be designed to detect and measure electrical, mechanical, chemical, electrochemical and/or electromechanical properties. For example, the system and method may incorporate a variety of sensor types, including but not limited to polymer and/or carbon black based nano composite array sensor and polymer and/or nanoparticles embedded in polymer based surface acoustic wave sensor. Sensor types may include functionalized and/or un-functionalized carbon nanotubes, such as, but not limited to polyaminobenzene sulfonic acid functionalized carbon nanotube, octadecylamine-functionalized carbon nanotubes, and amide functionalized carbon nanotubes in combination with additives such as, but not limited to triethylenediamine (TEDA), diethylenediamine or other amine derivatives, porphyrin or porphyrin derivatives, tris(ethlenediamine)nickel (II) chloride or other organometallic compounds, hydrogen peroxide, water/water vapor, and ozone. The sensor types may include metal oxide nanowires and/or nanoparticles such as, but not limited to $ZnO$, $SnO_2$, $In_2O_3$, $TiO_2$, $MgO$, $CdO$, $Ga_2O_3$, $Cu_2O$, and $WO_3$ in combination with additives such as, but not limited to triethylenediamine (TEDA), diehylenediamine, or other amine derivatives, porphyrin or porphyrin derivatives, tris(ethylenediamine)nickel (II) chloride or other organometallic compounds, hydrogen peroxide, water/water vapor, and ozone. The various modifications necessary to practice the method in any environment and with respect to any target agent of interest are within the contemplated scope of the present invention.

In one exemplary embodiment of the additive-enhanced detection system 10, and adhering to the exemplary application wherein cyanogen chloride (CK) is the detection target agent of a CNT technology-based sensor, the additive 22 may be triethylenediamine (TEDA). A significant limitation in the utility and application of CNT sensor technology is limited sensitivity, or the ability of CNTs to detect certain agents or concentration levels of agents of interest. For example, carbon nanotube-based sensor systems do not have the capacity to detect low, yet dangerous concentrations of cyanogen chloride (CK), a key agent of interest in the field of chemical warfare detection. It is known in the field of air purification that the removal of CK from an ambient environmental sample may be accomplished by impregnating activated carbons with an additive, such as triethylenediamine (TEDA). In this application, TEDA chemically reacts with CK, resulting in cyanic acid (HOCN), subsequently decomposing to carbon dioxide ($CO_2$) and ammonia ($NH_3$), accompanied by a series of complex side reactions (not involving TEDA) to form several persistent compounds. Reference: *Role of TEDA as an Activated Carbon Impregnate for the Removal of Cyanogen Chloride from Air Streams: Synergistic Effect with Cu(II)*; John J. Hahle, et al.; J. Phys. Chem. C; Vol. 114; 2010; pp. 20083-20090, incorporated herein by reference. When these reaction products are deposited over the surface of certain carbon nanotube-based sensors, as will be discussed further in this specification, the electrical properties of the sensors are altered. Therefore, by introducing TEDA to an environmental sample, the presence of very low concentrations of CK in the sample may be indicated by the response of the detection system to the reaction products.

To achieve an operational state, a means of producing the flow of an ambient environment sample through the flow path 12 is required. This flow may be accomplished either by forcing the ambient environment sample into the intake 14, or by drawing the ambient environment sample out of the exhaust 16. The flow may be achieved by placing the additive-enhanced detection system 10 into an ambient environment fluid stream, for example by mounting the additive-enhanced detection system 10 on a moving vehicle. The flow may also be achieved by an active means such as a pump (not shown). The active means or pump may be integrated proximal to the intake 14 and be designed and configured to force an ambient environment sample into the flow path 12. Alternatively, the active means or pump may be integrated proximal to the exhaust 16 and be designed and configured to draw an environmental sample through the flow path 12.

The flow rate may be, but is not limited to a range from 1 cc per minute to 3,000 cc per minute.

In alternative embodiments of the system, a plurality of additives may be employed, in one or more additive reservoirs, to enable an additive-enhanced detection system to detect a plurality of target agents, or to enhance the specificity of the detection system.

In one embodiment, sensor A 32 may be identical to sensor B 36. In the method of use of the additive-enhanced detection system 10, sensor A 32 may be exposed to a sample of the ambient environment with the additive 22 added to the sample, while sensor B 36 may be exposed to a sample of the ambient environment without the additive 22. Because the additive-enhanced detection system 10 is designed to detect the presence of a chemical and/or biological agent that may only be detected in the presence of an additive 22, the comparison of the response over time of sensor A 32 to the response over time of sensor B 36 may provide an indication of the presence of the detection target agent.

In an alternative embodiment, the flow path 12 may be separated into two independent flow paths, one designed to direct the flow of an ambient environment sample to sensor A 32, and the other designed to direct the flow of an ambient environmental sample to sensor B 36. In this alternative embodiment, each of the two independent flow paths may have its own separate intake and exhaust. However, the embodiments that have a single intake have the advantage of ensuring that the sensors may be exposed to the same ambient environment sample.

Figure 2:
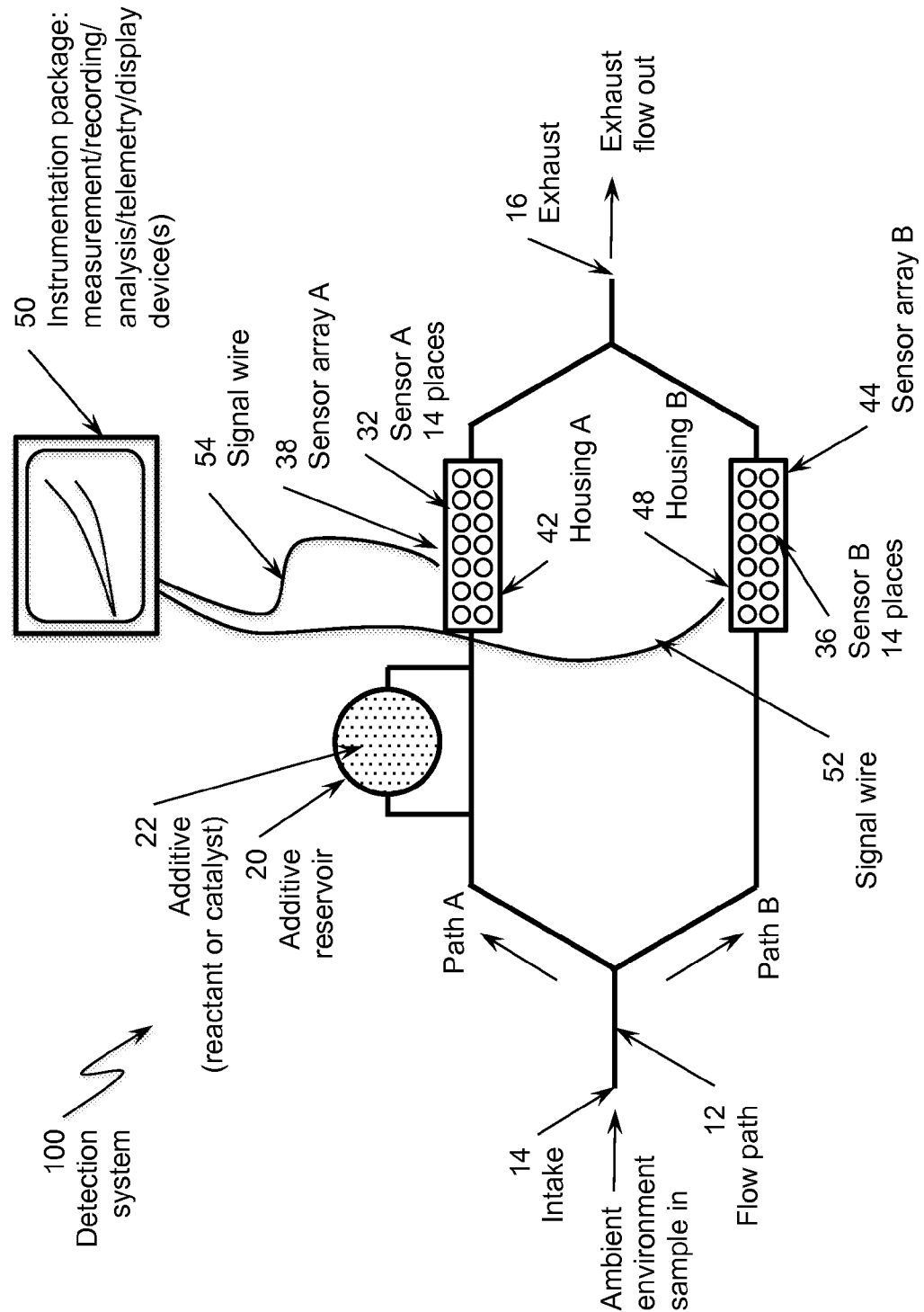
FIG. 2 presents a block diagram of a system for detecting chemical and/or biological agents, according to another exemplary embodiment of the present invention.

FIG. 2 presents a block diagram of an additive-enhanced detection system 100 according to another alternative embodiment of the present invention. This alternative embodiment may be similar in design, configuration and function to the embodiment of an additive-enhanced detection system 10 illustrated in FIG. 1, except that the sensors 32/36 of embodiment 10 are replaced by sensor arrays 38/44, respectively. Incorporation of a plurality of sensors into a sensor array may provide system redundancy and reliability, and a more robust data set. Further, it may be desirable to incorporate sensors of more than one design into an array. Incorporation of a plurality of sensor types into a sensor array may enhance system selectivity and sensitivity, prevent false alerts, and may enable detection of the presence of more than one target chemical and/or biological agent. It is within the contemplated scope of the present invention that a plurality of sensors may be incorporated into one or more sensor arrays. It is also within the contemplated scope of the present invention that two or more sensors types may be incorporated into a sensor array.

As shown in FIG. 2, a housing B 48 may be integrated into, and in fluid communication with Path B. A sensor array B 44, comprising a plurality of sensors B 36, may be contained within housing B 48 such that sensor array B 44 may be exposed to the ambient environment sample as the sample flows through Path B. Sensor array B 44 may be electrically connected, by means of an electrically conductive wire 52, to one or more devices 50 designed and configured to measure, record, display and/or analyze an electrical property of sensors B 36 over time.

Similarly, a housing A 42 may be integrated into, and in fluid communication with Path A. A sensor array A 38 may be contained within housing A 42 such that the sensor array A 38 may be exposed to the ambient environment sample as the sample flows through Path A. Sensor array A 42 may be connected, by means of an electrically conductive wire 54 to one or more devices 50 designed and configured to measure, record, display and/or analyze an electrical property of sensors A 32 over time.

In alternative embodiments, the system may comprise more than two flow paths. Each of the flow paths may incorporate identical sensors or sensor arrays or, alternatively, each flow path may incorporate a sensor or sensor array that may be selected to provide system selectivity and/or sensitivity with respect to one or more particular chemical and/or biological agent. Further, each flow path may incorporate one or more additive reservoirs and additives that may similarly be selected to provide system selectivity and/or sensitivity with respect to one or more particular chemical and/or biological agent. A particular embodiment of an additive-enhanced detection system may or may not have a control flow path, a control flow path being defined as a flow path in which no additive may be introduced.

Figure 3:
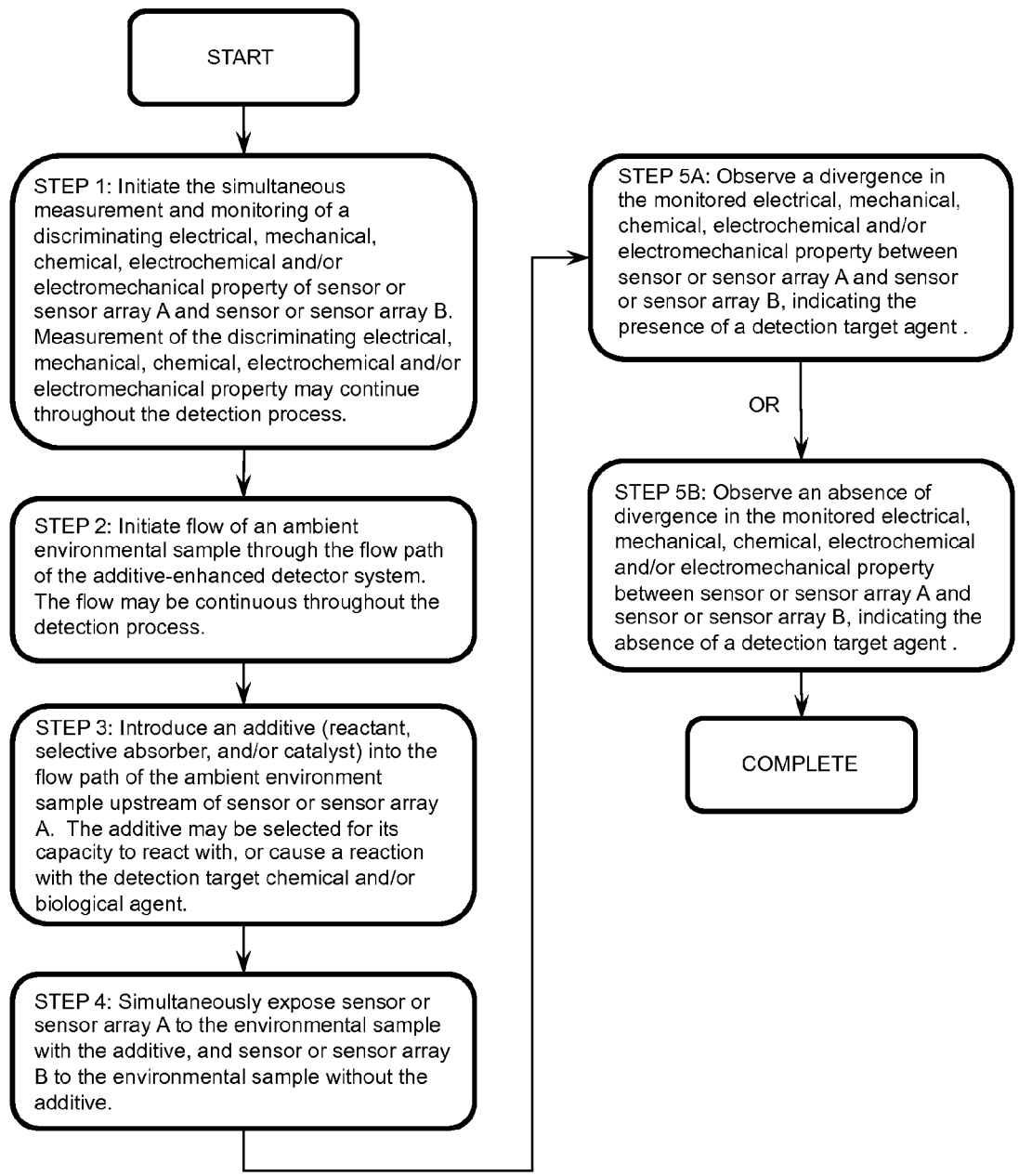
FIG. 3 presents a flowchart showing the steps of a method for detecting chemical and/or biological agents employing the system of FIG. 1 or FIG. 2, according to one exemplary embodiment of the present invention.

FIG. 3 presents a flowchart of an additive-enhanced detection method of using the additive-enhanced detection system 10 of FIG. 1, or the additive-enhanced detection system 100 of FIG. 2, according to one embodiment of the invention, comprising the following steps.

Step 1: Initiate the simultaneous measurement and monitoring of a discriminating electrical, mechanical, chemical, electrochemical and/or electromechanical property of sensor or sensor array A and sensor or sensor array B. Measurement of the discriminating electrical, mechanical, chemical, electrochemical and/or electromechanical property may continue throughout the detection process.

Step 2: Initiate flow of an ambient environmental sample through the flow path of the additive-enhanced detector system. The flow may be continuous throughout the detection process.

Step 3: Introduce an additive (reactant, selective absorber, and/or catalyst) into the flow path of the ambient environment sample upstream of sensor or sensor array A. The additive may be selected for its capacity to react with, or cause a reaction with the detection target chemical and/or biological agent.

Step 4: Simultaneously expose sensor or sensor array A to the environmental sample with the additive, and sensor or sensor array B to the environmental sample without the additive.

Step 5A: Observe a divergence in the monitored electrical, mechanical, chemical, electrochemical and/or electromechanical property between sensor or sensor array A and sensor or sensor array B, indicating the presence of a detection target agent; or Step 5B: Observe an absence of divergence in the monitored electrical, mechanical, chemical, electrochemical and/or electromechanical property between sensor or sensor array A and sensor or sensor array B, indicating the absence of a detection target agent.

The method of using the additive-enhanced detection system 100 of FIG. 2 may be identical to the method of using the additive-enhanced detection system 10 of FIG. 1, except that sensor array A 38 and sensor array B 44 may be substituted for sensor A 32 and sensor B 36, respectively.

In one exemplary embodiment of the method, the electrical property to be measured may be resistance. Alternative embodiments may measure other electrical properties, such as conductance, capacitance, or voltage. Still other alternative embodiments may measure mechanical, chemical, electrochemical and/or electromechanical properties.

Figure 4:
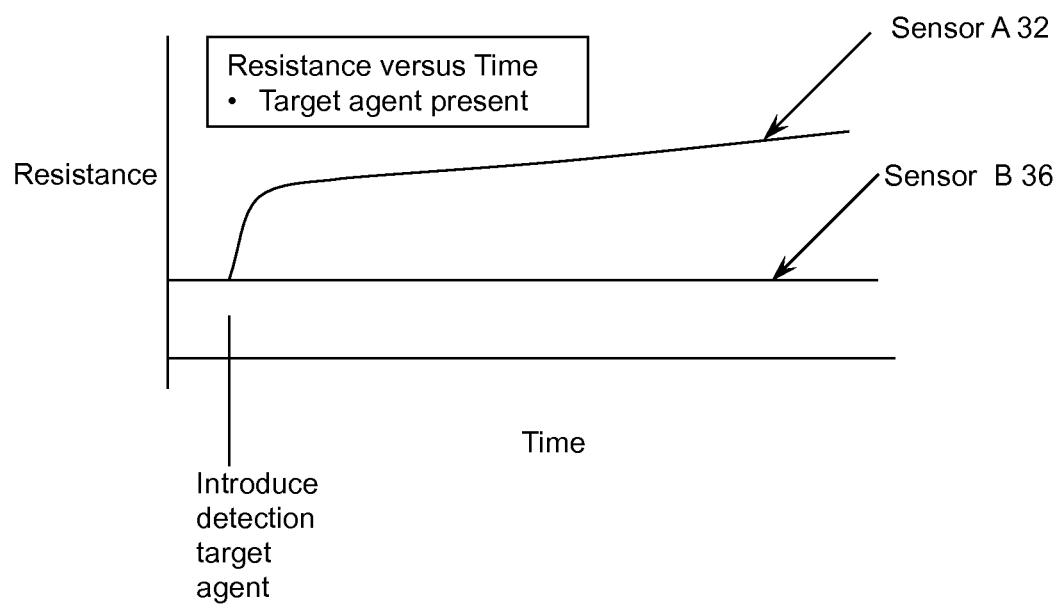
FIG. 4 presents an illustrative example of a display of the output data of the method of FIG. 3, according to one exemplary embodiment of the present invention.

FIG. 4 presents an illustrative example of a display of the output information of the additive-enhanced detection method of FIG. 3, wherein the monitored property is electrical resistance, showing a divergence in the monitored property between sensor A 32 and sensor B 36 in the presence of a detection target agent.

In alternative embodiments of the method, a plurality of additives may be employed, in one or more additive reservoirs, to enable an additive-enhanced detection method to detect a plurality of target agents, or to enhance the specificity of the detection system.

Figure 5:
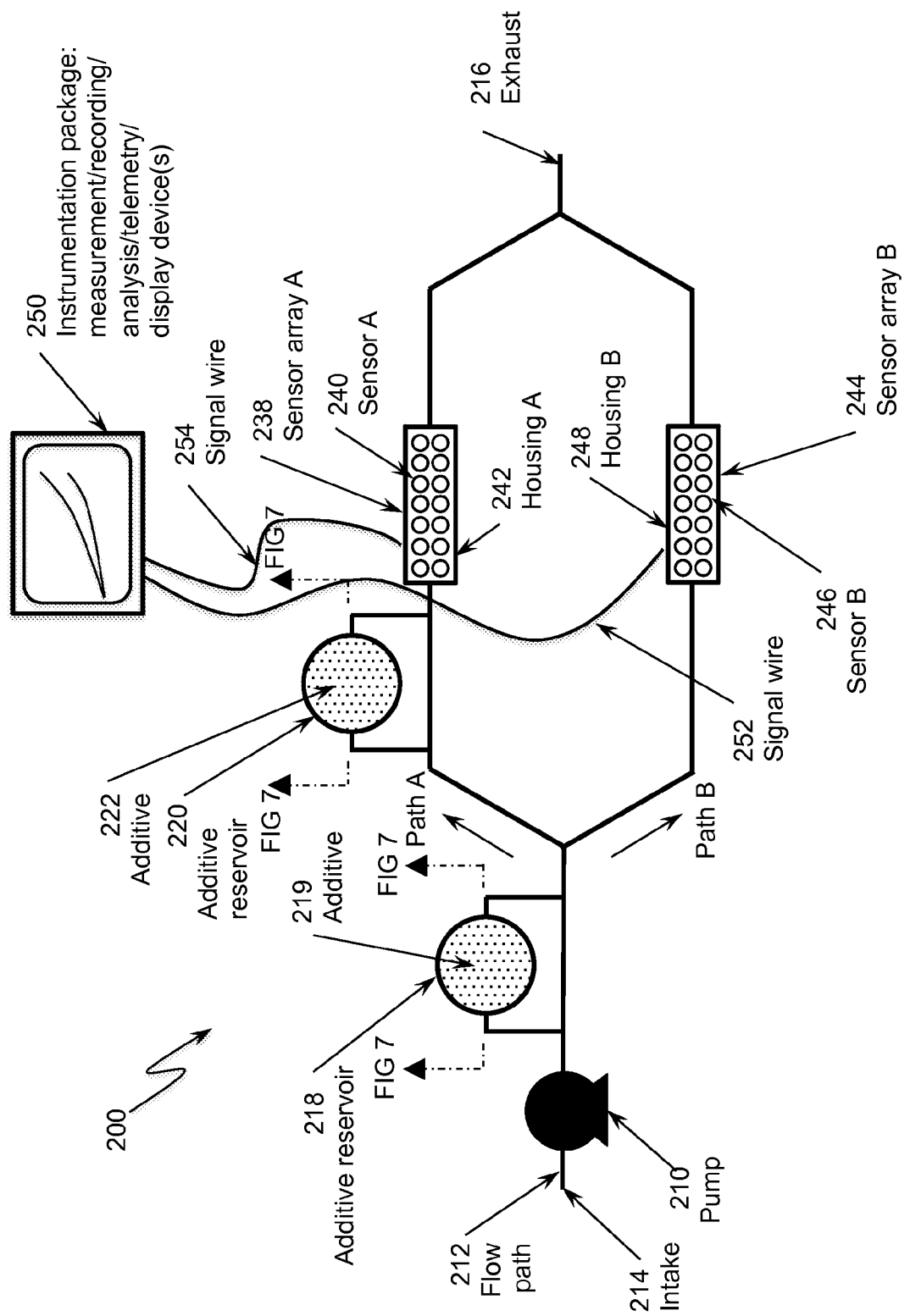
FIG. 5 presents a block diagram of a system for detecting chemical and/or biological agents, according to another exemplary embodiment of the present invention.
Figure 6:
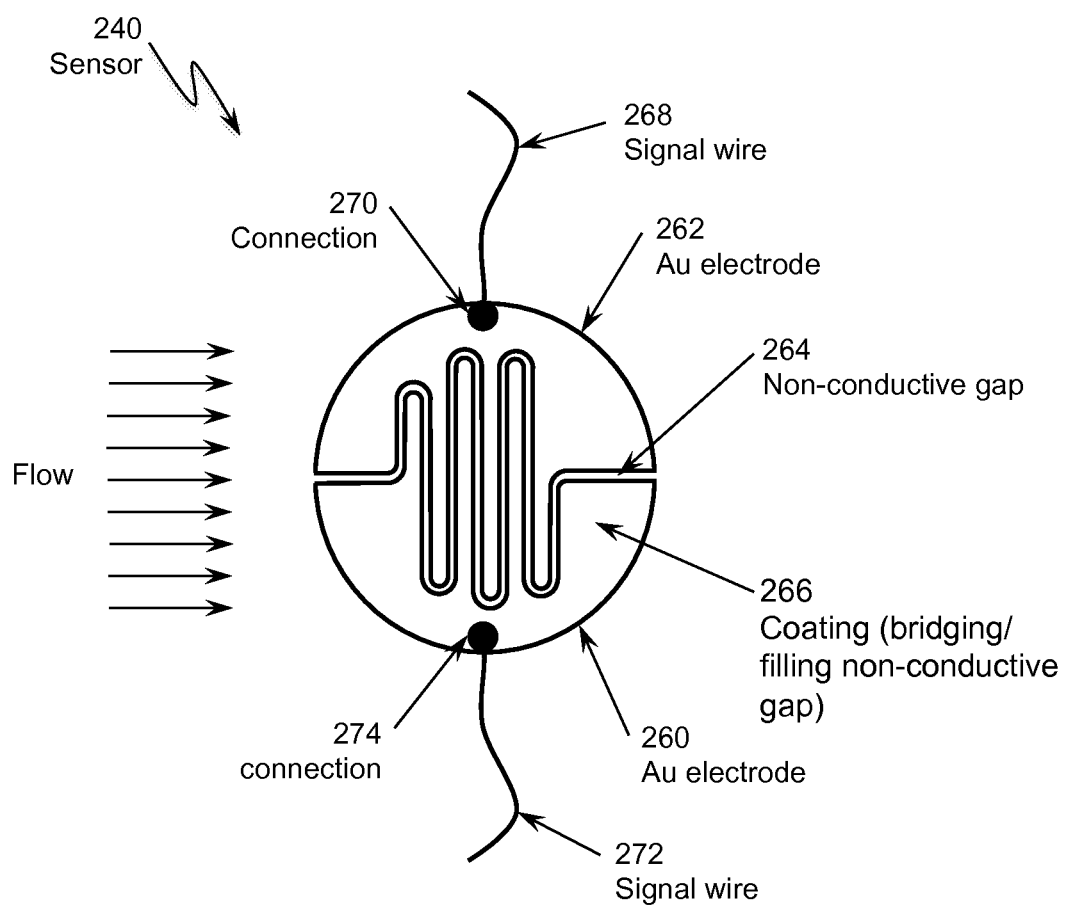
FIG. 6 presents a detail view of a sensor of the system of FIG. 5, according to one embodiment of the present invention.
Figure 7A:
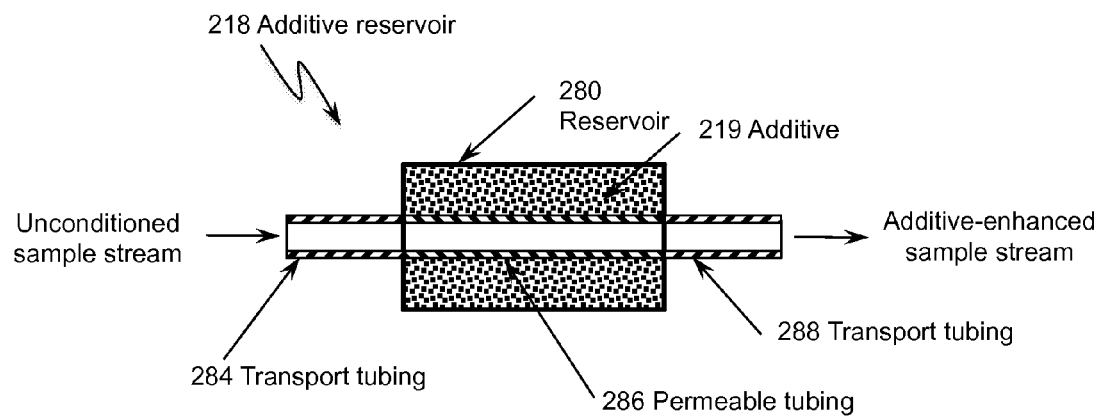
FIG. 7 presents cross-sectional detail views of two additive reservoirs of the system of FIG. 5, according to two alternative embodiments of the present invention.
Figure 7B:
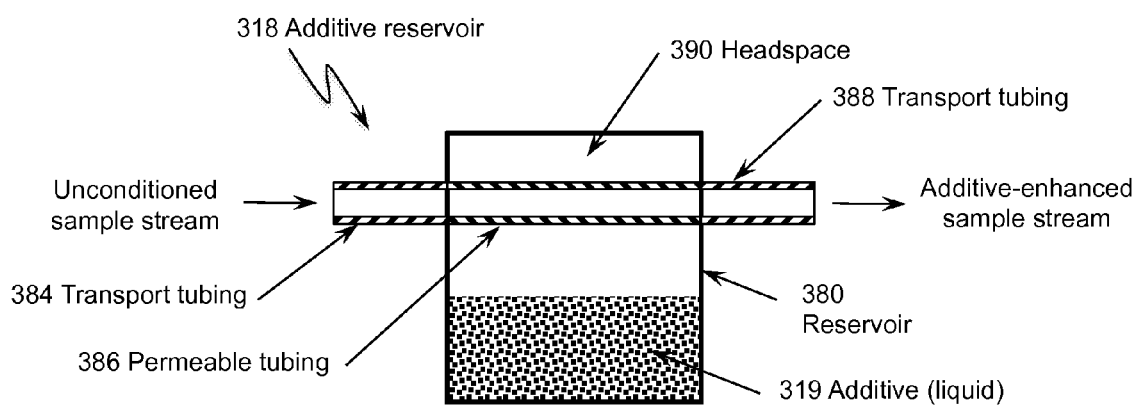
Figure 8:
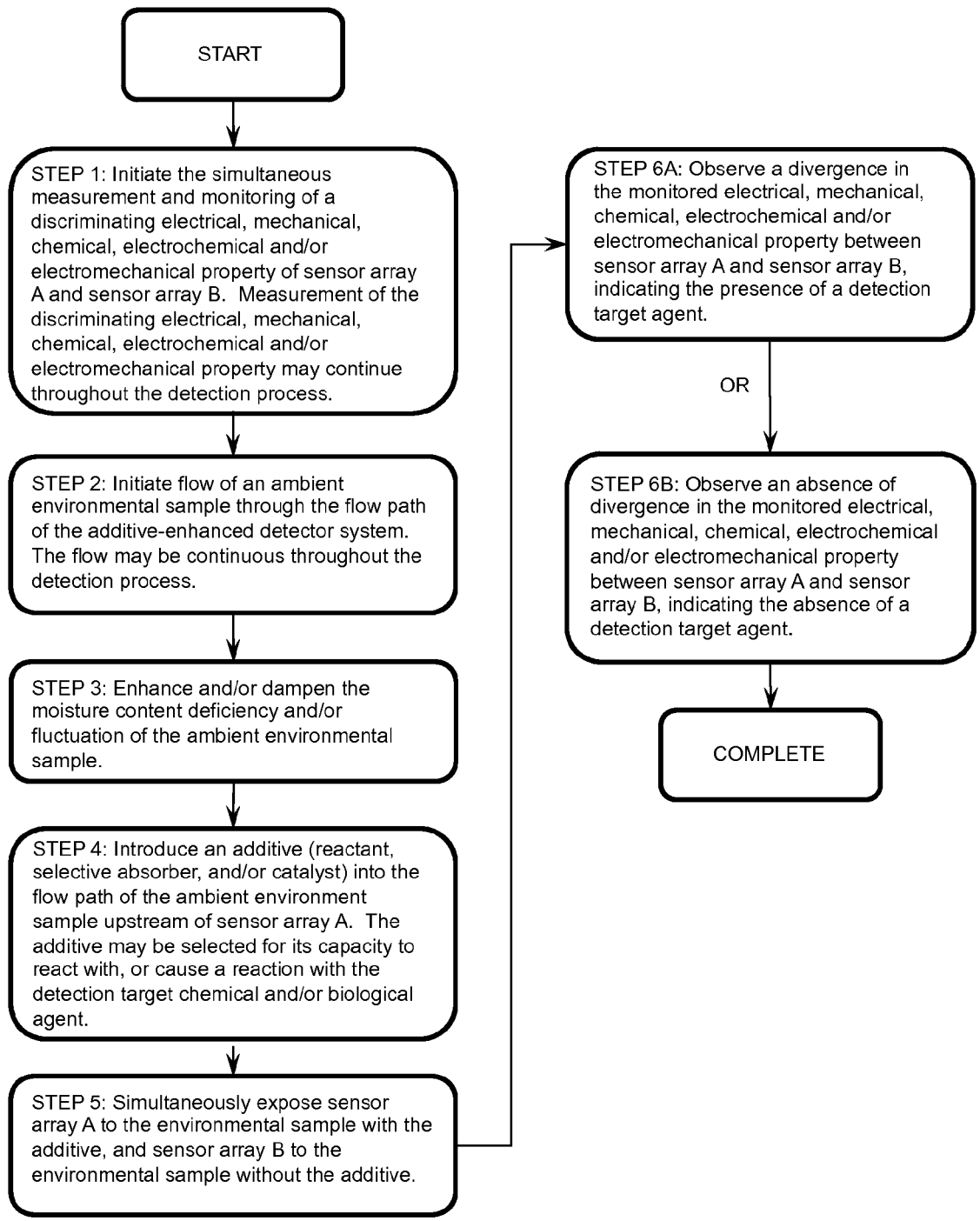
FIG. 8 presents a flowchart showing the steps of a method for detecting chemical and/or biological agents employing the system of FIG. 5, according to one embodiment of the present invention.
Figure 9:
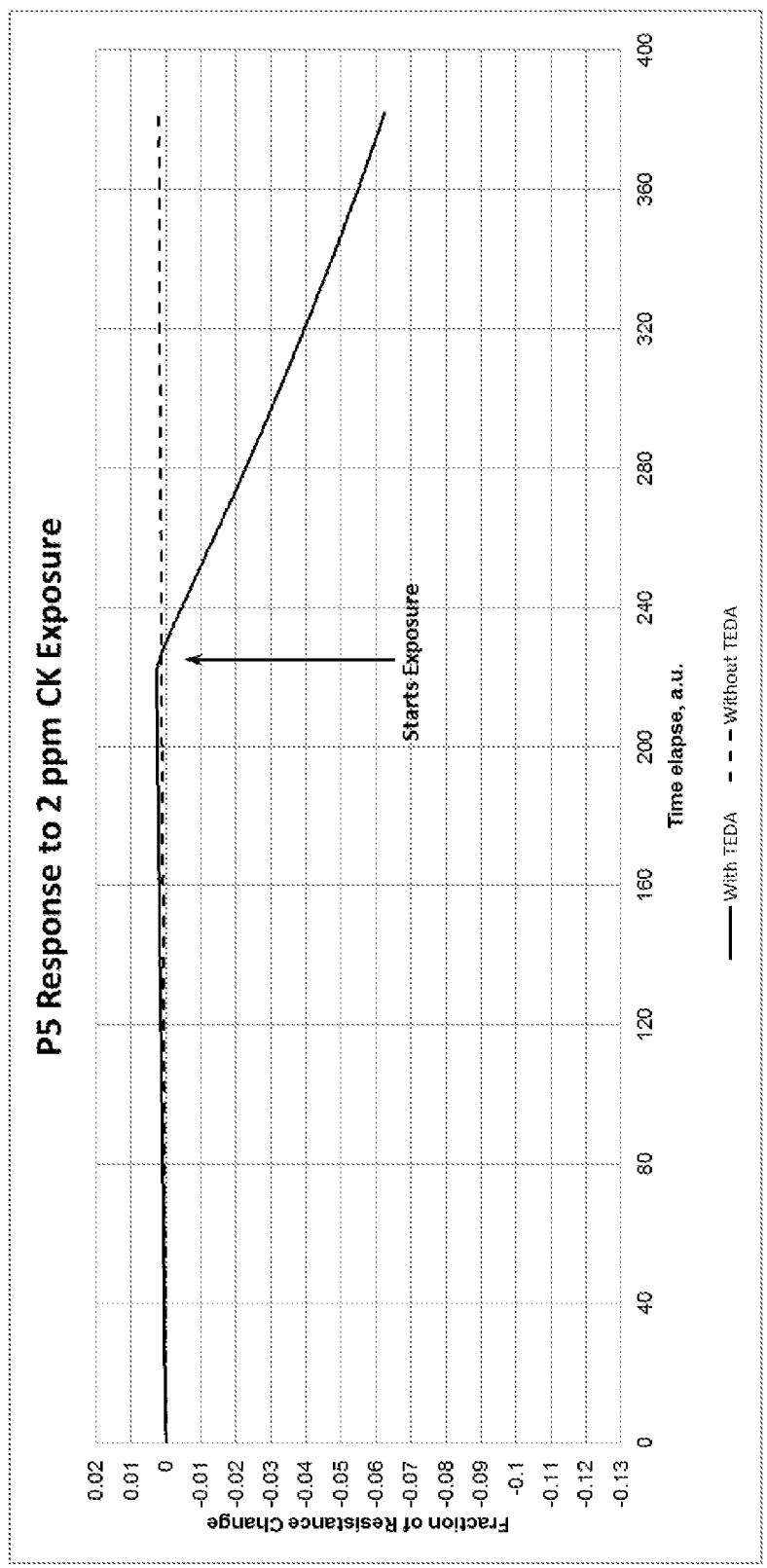
FIG. 9 presents an illustrative example of a display of the output data of the method of FIG. 8, according to one exemplary embodiment of the present invention.

FIG. 5 presents a block diagram of an additive-enhanced detection system 200 according to an exemplary embodiment of the present invention, comprising a flow path 212 that may be designed and configured to direct the flow of samples of an ambient environment into which the additive-enhanced detection system 200 is placed. The flow path 212 may have an intake 214 designed to enable a sample of the ambient environment to enter the flow path 212, and an exhaust 216 designed to enable the ambient environment sample to exit the flow path 212.

Downstream of the intake 214, the flow path 212 may be separated into Path A and Path B, as illustrated in FIG. 5. A housing B 248 may be integrated into, and in fluid communication with Path B. A sensor array B 244, comprising a plurality of sensors B 246, may be contained within housing B 248 such that sensor array B 244 may be exposed to the ambient environment sample as the sample flows through Path B. Sensor array B 244 may be electrically connected, by means of an electrically conductive signal wire 252, to one or more devices 250 designed and configured to measure, record, display and/or analyze an electrical, mechanical, chemical, electrochemical and/or electromechanical property of sensors B 246 over time.

A housing A 242 may be integrated into, and in fluid communication with Path A. A sensor array A 238, comprising a plurality of sensors A 240, may be contained within housing A 242 such that the sensor array A 238 may be exposed to the ambient environment sample as the sample flows through Path A. Sensor array A 238 may be connected, by means of an electrically conductive signal wire 254 to one or more devices 250 designed and configured to measure, record, display and/or analyze an electrical, mechanical, chemical, electrochemical and/or electromechanical property of sensors A 240 over time.

An additive reservoir 220 may be integrated into, and in fluid communication with Path A upstream of sensor array A 238. The additive reservoir 220 may contain an additive 222, and may be designed to introduce the additive 222 into Path A, thereby causing the additive to be mixed with the ambient environment sample as the sample flows through Path A. The additive 222 may be a reactant, selective absorber, and/or a catalyst selected for its capacity to cause and/or participate in a chemical reaction, the reaction product of which may be detected by the sensor array A 238, when mixed with the ambient environment sample. The additive 222 may be in solid, liquid or vapor form. The additive reservoir 220 may perform the mixing function by, any practical or useful means, including but not limited to a liquid bath, chemical jet, positive pressure pump, heat evaporation, capillary action, siphon suction, or Bernoulli's principle. Per Bernoulli's principle, the additive is delivered to the sensor or sensor array without use of additional energy. The amount of additive delivered to the sensor or sensor array is controlled by saturated vapor pressure of the additive and the flow rate of the sample of an ambient environment.

An instrumentation package 250 may include one or more devices for measuring changes in an electrical, mechanical, chemical, electrochemical and/or electromechanical property (such as current, capacity, voltage or resistance across a sensor), recording measured and/or calculated data, analyzing measured and/or calculated data, telemetry of measured and/or calculated data to a remote user, and displaying measured and/or calculated data. The one or more devices may be packaged individually or integrated into one or more subsystems.

Non-limiting examples of devices that may be incorporated into the instrumentation package 250 include the following. A device for measuring changes in an electrical property may be an ohmmeter, an amp meter, a Faraday plate or a photodiode. A device for recording measured and/or calculated data may be a machine-readable memory. A device for analyzing measured and/or calculated data may be a computer processor or microprocessor in combination with logic, commands and algorithms stored in on a machine-readable medium. A device for telemetry of measured and/or calculated data may be a transmitter or a transceiver. A device for displaying measured and/or calculated data may include a video screen, a printing device, a photographic device, or any useful medium for communicating system output. The instrumentation package 250 may incorporate a means of providing power to the various devices, such as a battery and/or a power generation means such as a solar power generation device.

To achieve an operational state, a means of producing the flow of an ambient environment sample through the flow path 212 is required. This flow may be accomplished either by forcing the ambient environment sample into the intake 214, or by drawing the ambient environment sample out of the exhaust 216. The flow may be achieved by placing the additive-enhanced detector 200 into an ambient environment fluid stream, for example by mounting the additive-enhanced detector 200 on a moving vehicle. The flow may also be achieved by an active means such as a pump 210. The active means or pump 210 may integrated proximal to the intake 214 and be designed and configured to force an ambient environment sample into the flow path 212. Alternatively, the active means or pump 210 may be integrated proximal to the exhaust 216 and be designed and configured to draw an environmental sample through the flow path 212.

The flow rate may be, but is not limited to a range from 1 cc per minute to 3,000 cc per minute.

In one preferred embodiment, sensor array A 238 may be identical to sensor array B 244. In the method of use of the additive-enhanced detection system 200, sensor array A 238 may be exposed to a sample of the ambient environment with additive 222 added to the sample, while sensor array B 244 may be exposed to a sample of the ambient environment without additive 222. The comparison of the response over time of sensor array A 238 to the response over time of sensor array B 244 may provide an indication of the presence of the detection target agent.

Figure 10A:
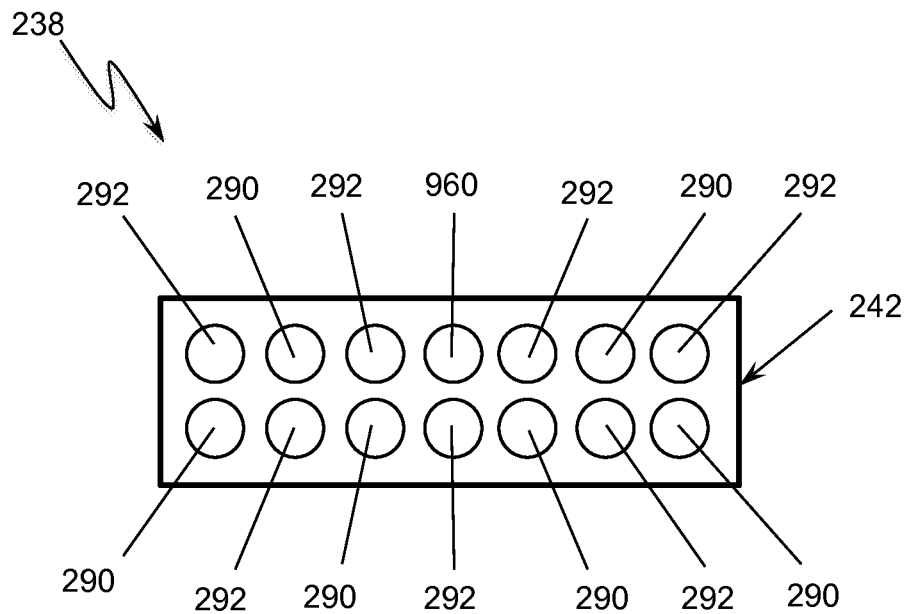
FIG. 10 presents detail schematic views of multi-type sensor arrays that may be incorporated into the system of FIG. 5, according to another embodiment of the present invention.
Figure 10B:
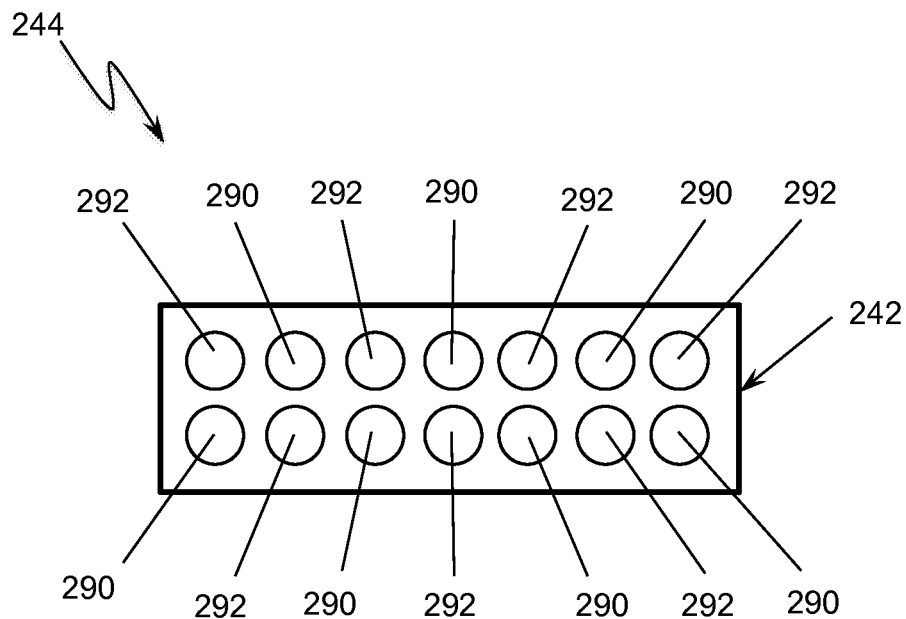
Figure 11A:
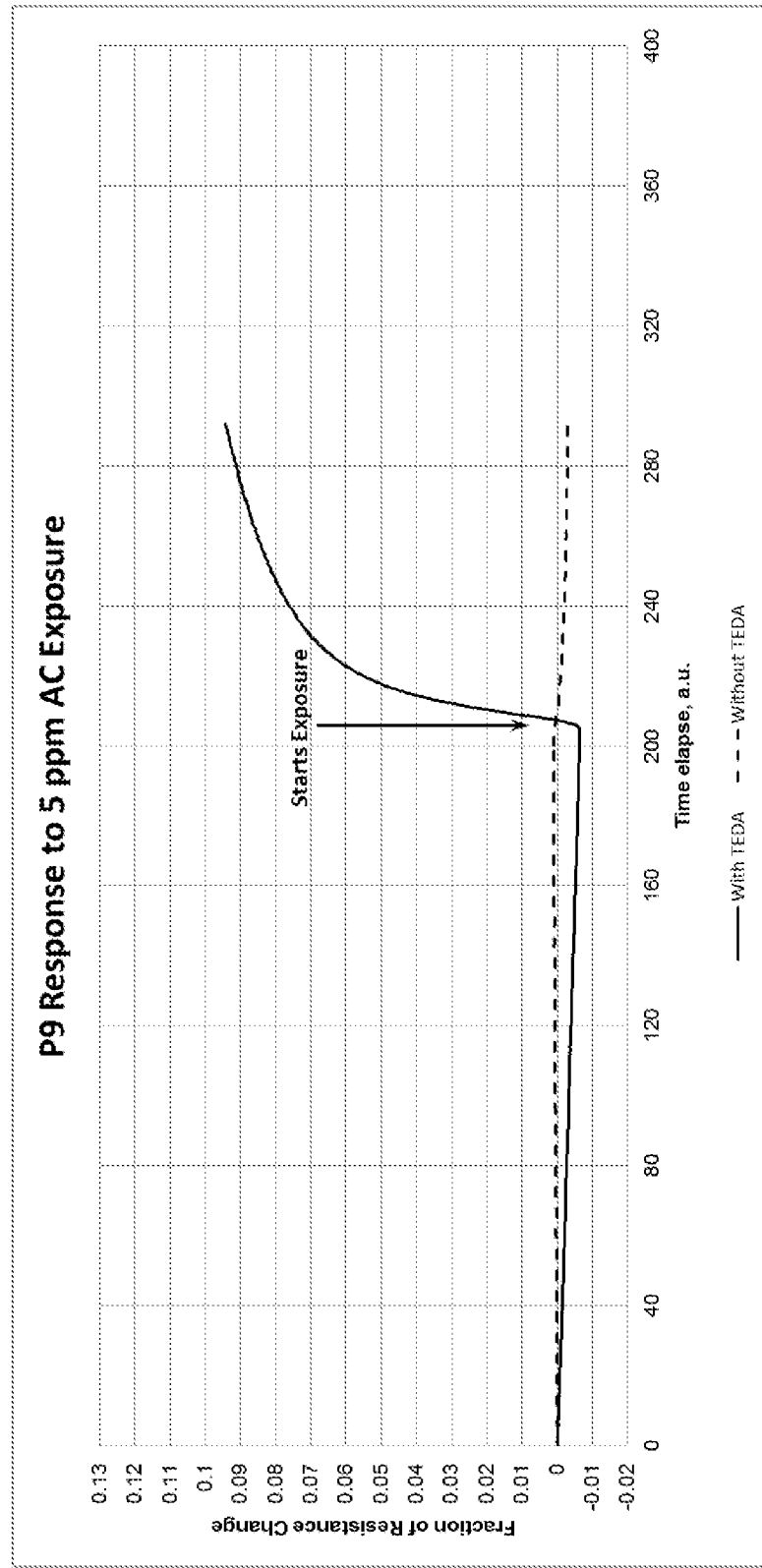
FIG. 11 presents an illustrative example of a display of the output data of the system of FIG. 5, incorporating the multi-type sensor arrays of FIG. 10, upon exposure to hydrogen cyanide (AC), according to one exemplary embodiment of the present invention.
Figure 11B:
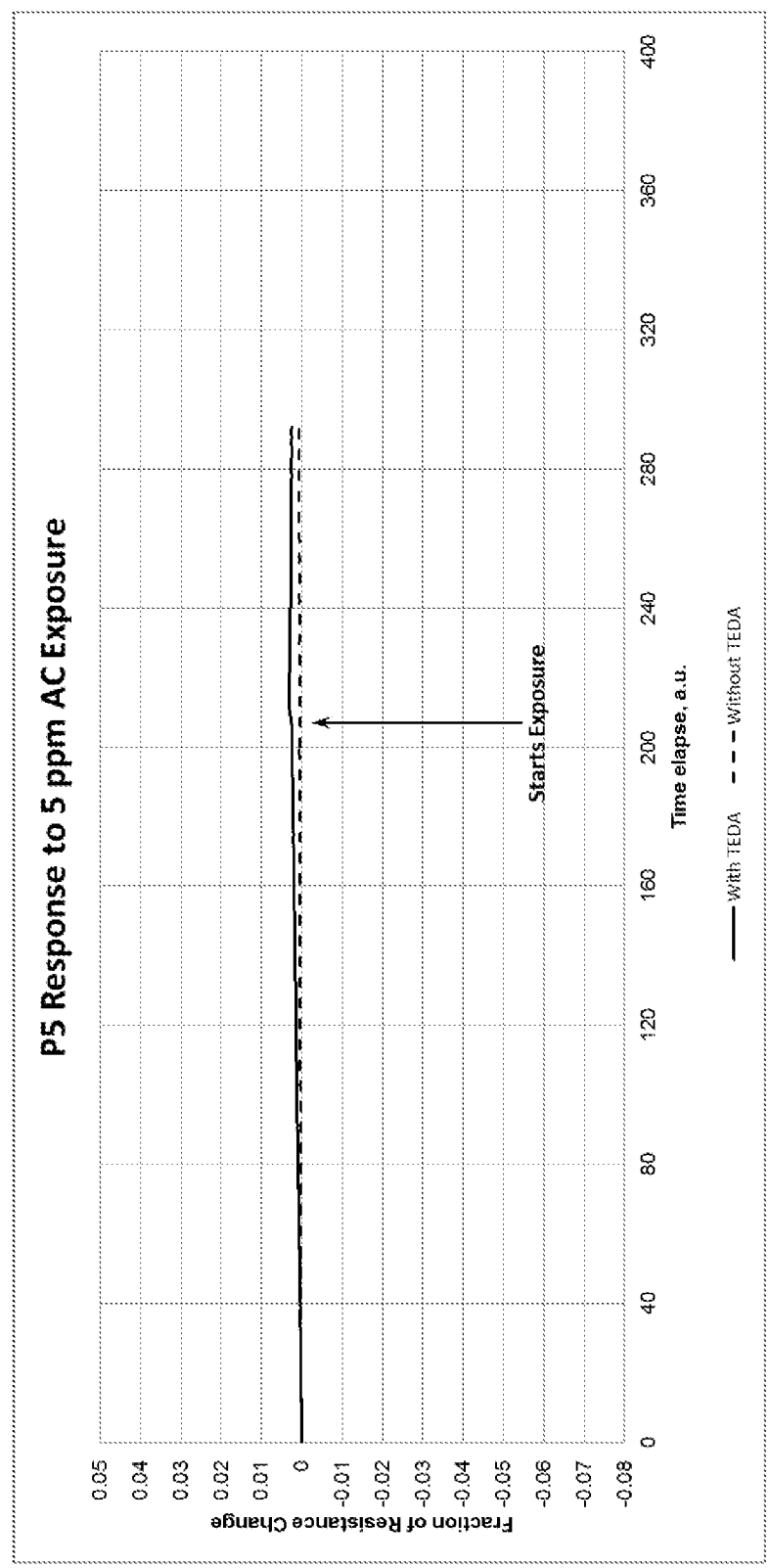
Figure 12A:
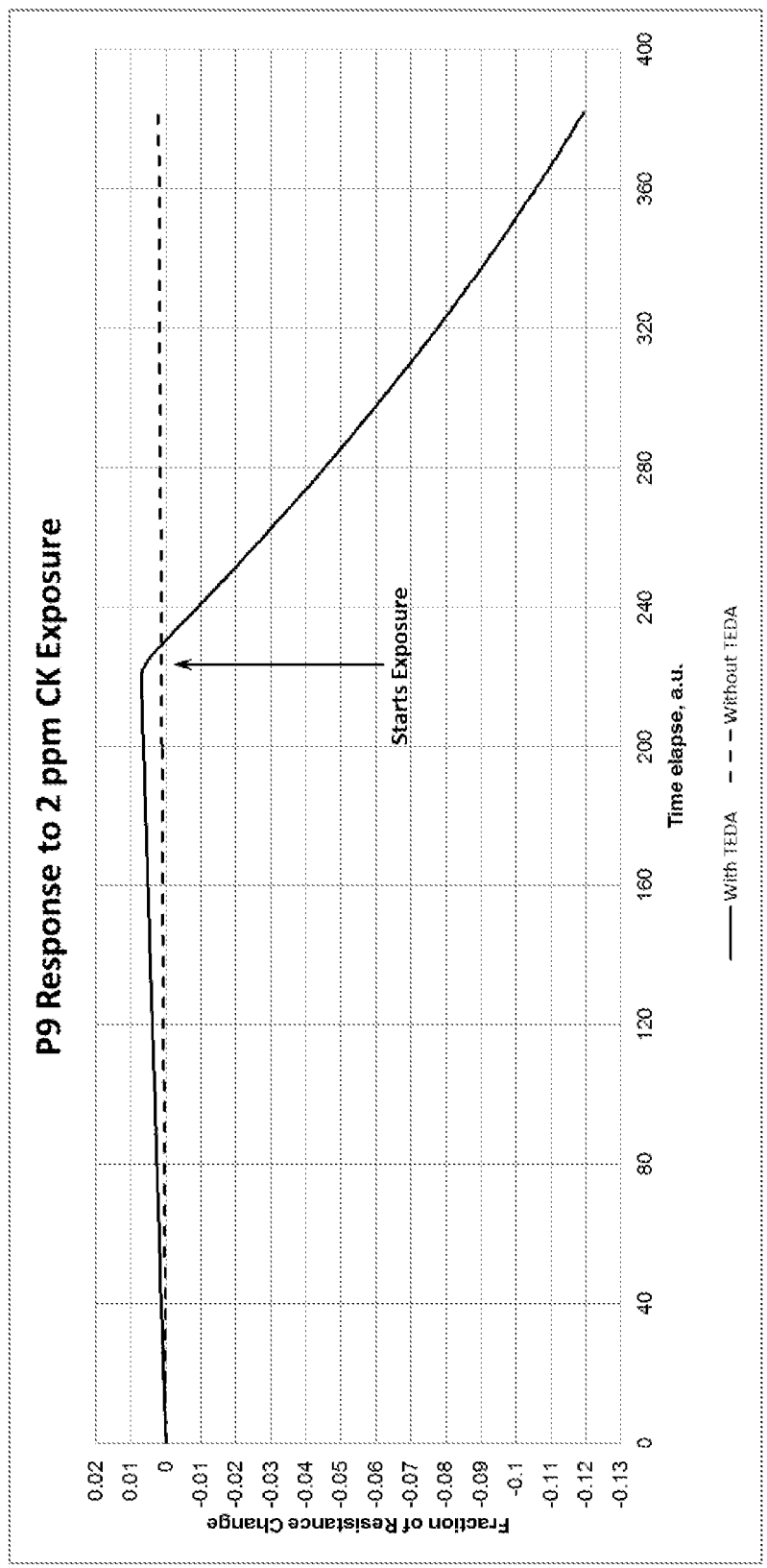
FIG. 12 presents an illustrative example of a display of the output data of the system of FIG. 5, incorporating the multi-type sensor arrays of FIG. 10, upon exposure to cyanogen chloride (CK), according to one exemplary embodiment of the present invention.
Figure 12B:
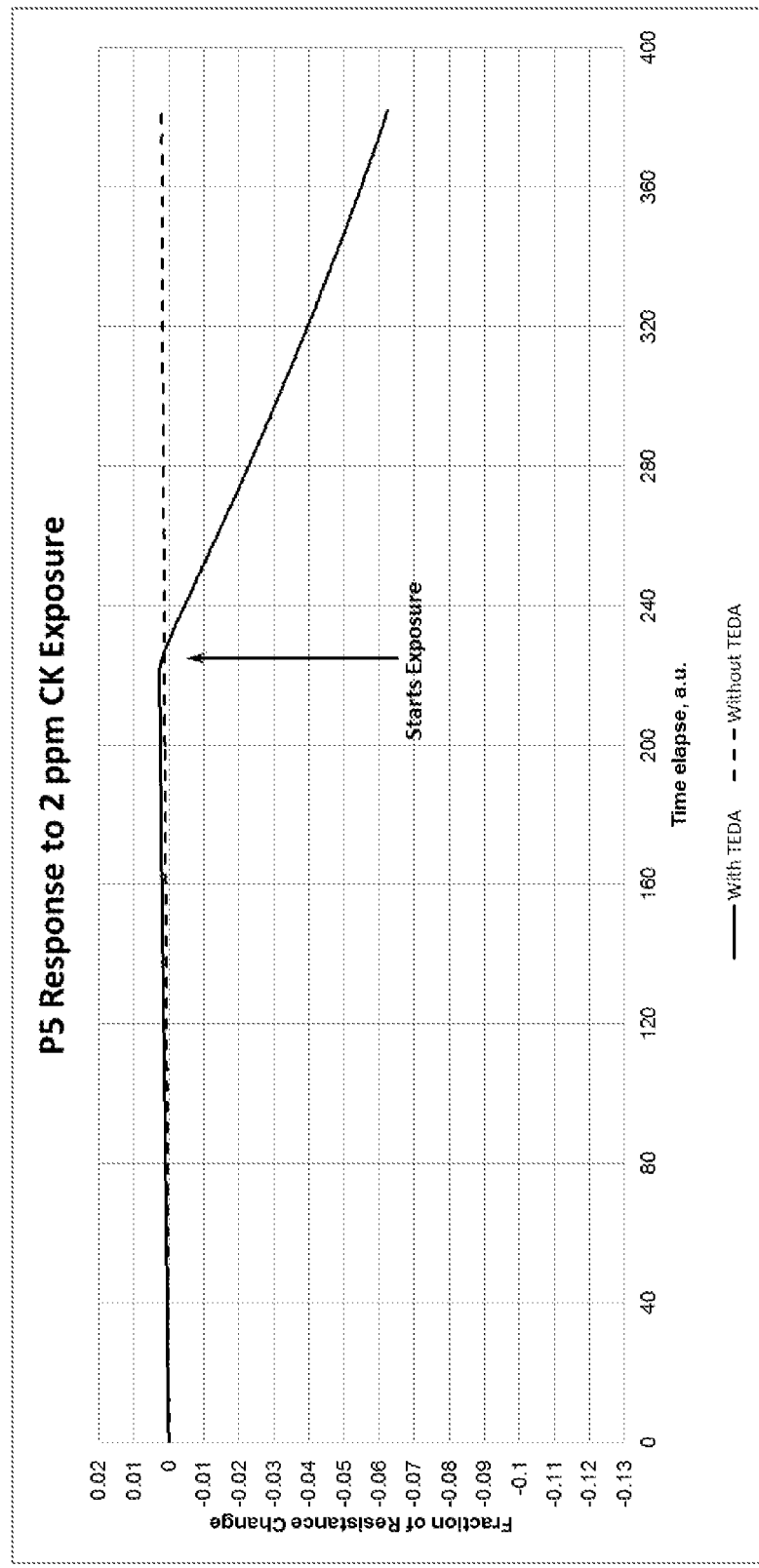
Figure 13A:
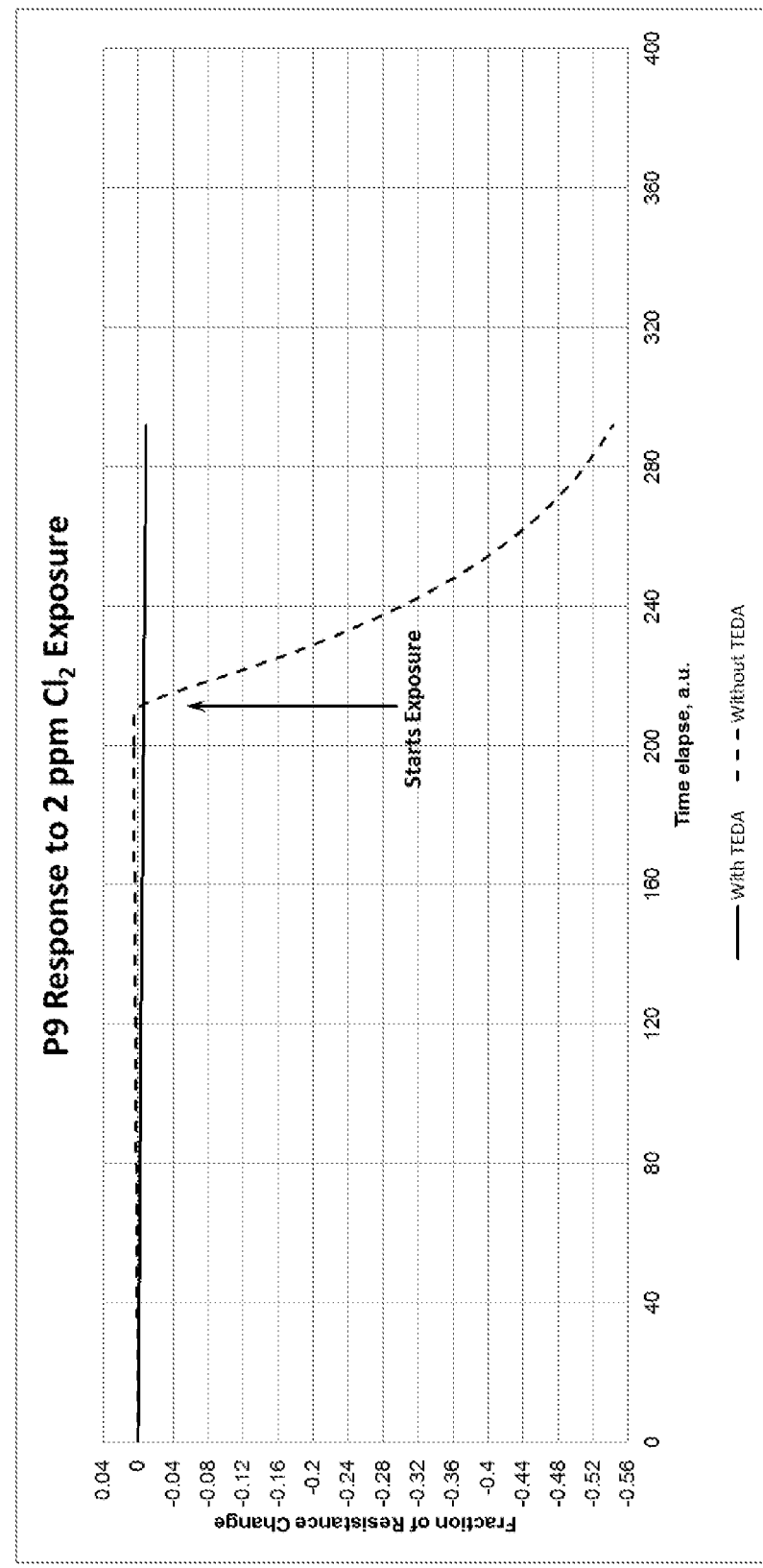
FIG. 13 presents an illustrative example of a display of the output data of the system of FIG. 5, incorporating the multi-type sensor arrays of FIG. 10, upon exposure to chloride gas ($Cl_2$), according to one exemplary embodiment of the present invention.
Figure 13B:
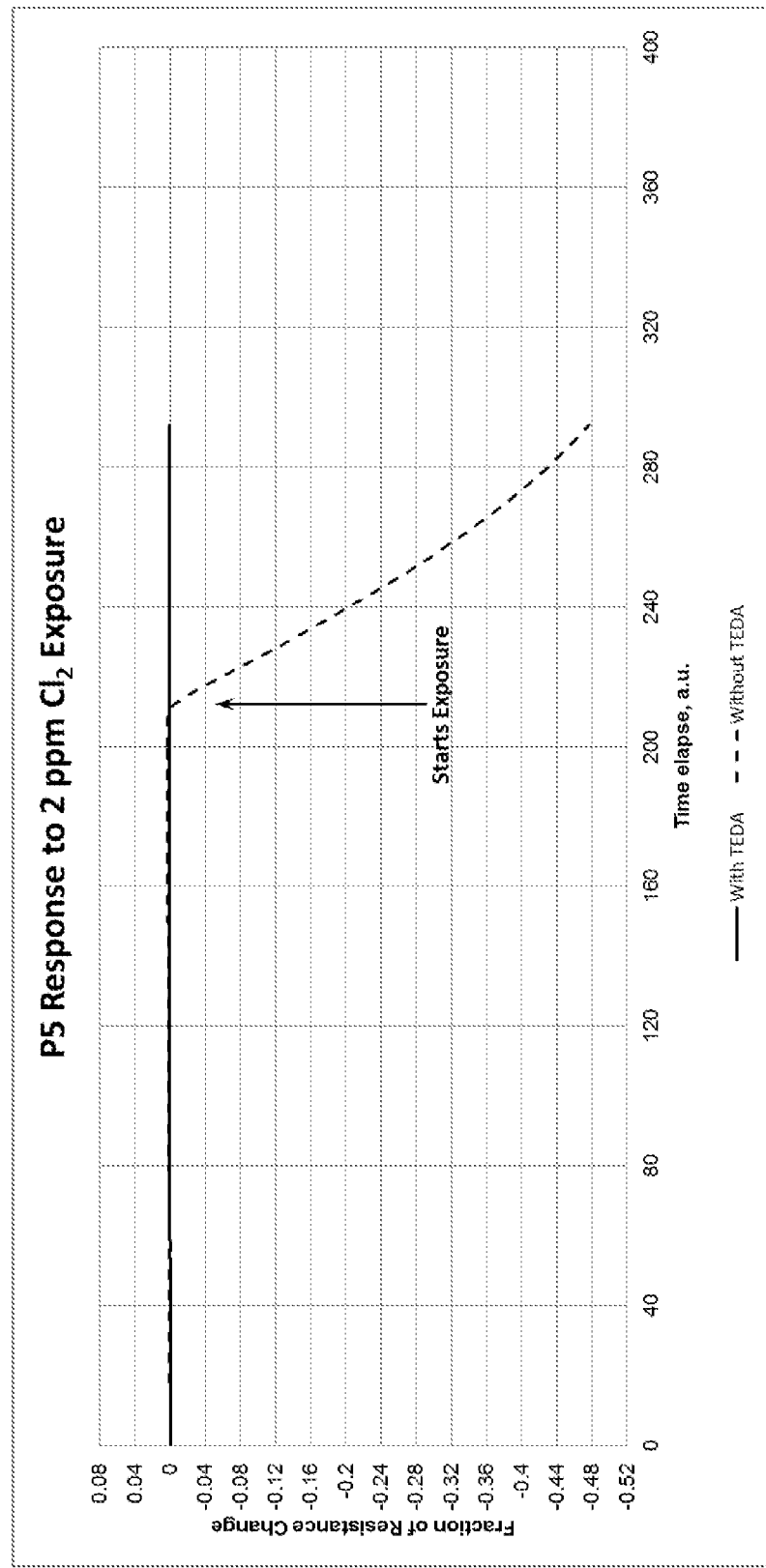
Figure 14A:
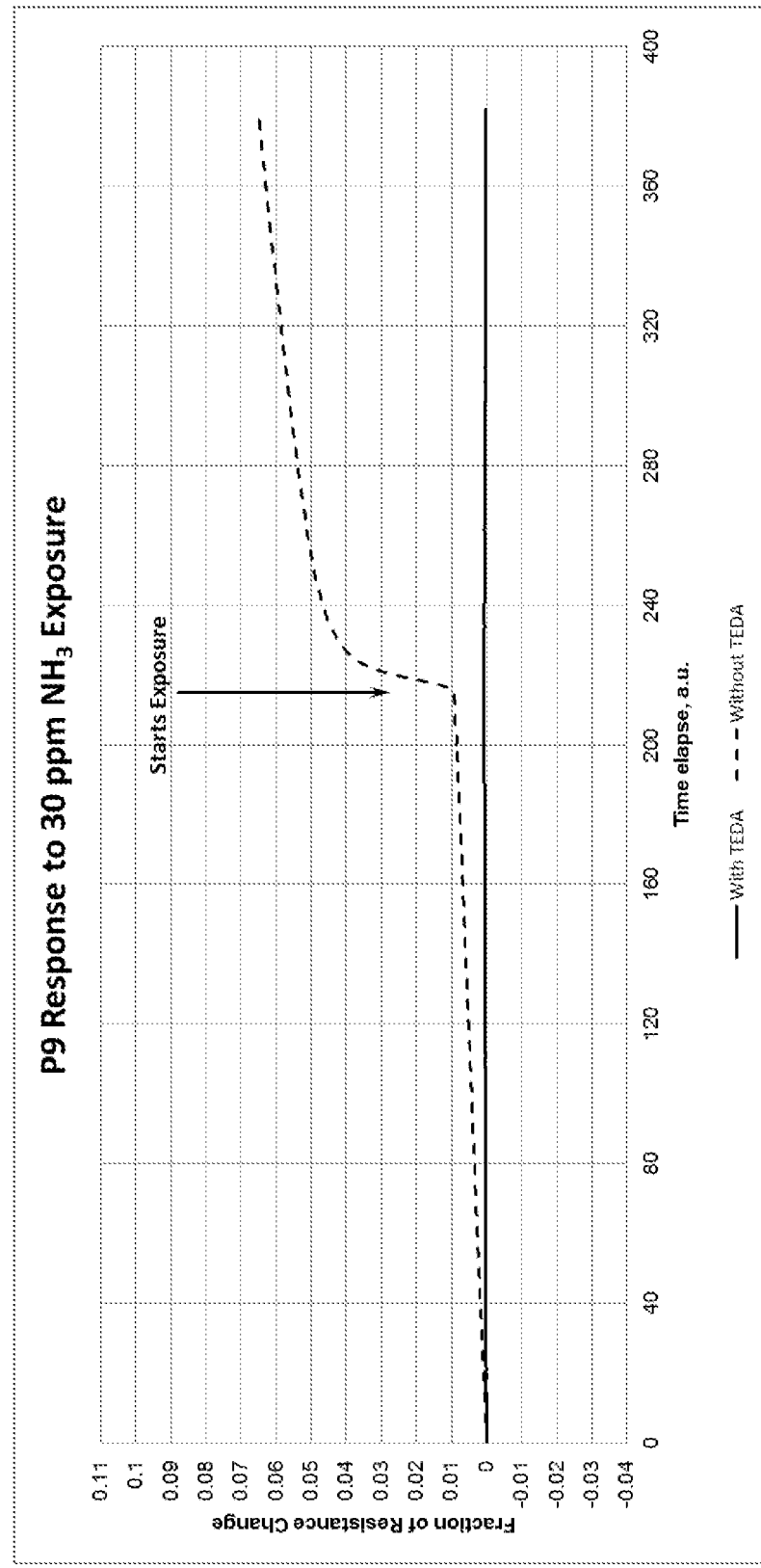
FIG. 14 presents an illustrative example of a display of the output data of the system of FIG. 5, incorporating the multi-type sensor arrays of FIG. 10, upon exposure to ammonia gas ($NH_3$), according to one exemplary embodiment of the present invention.
Figure 14B:
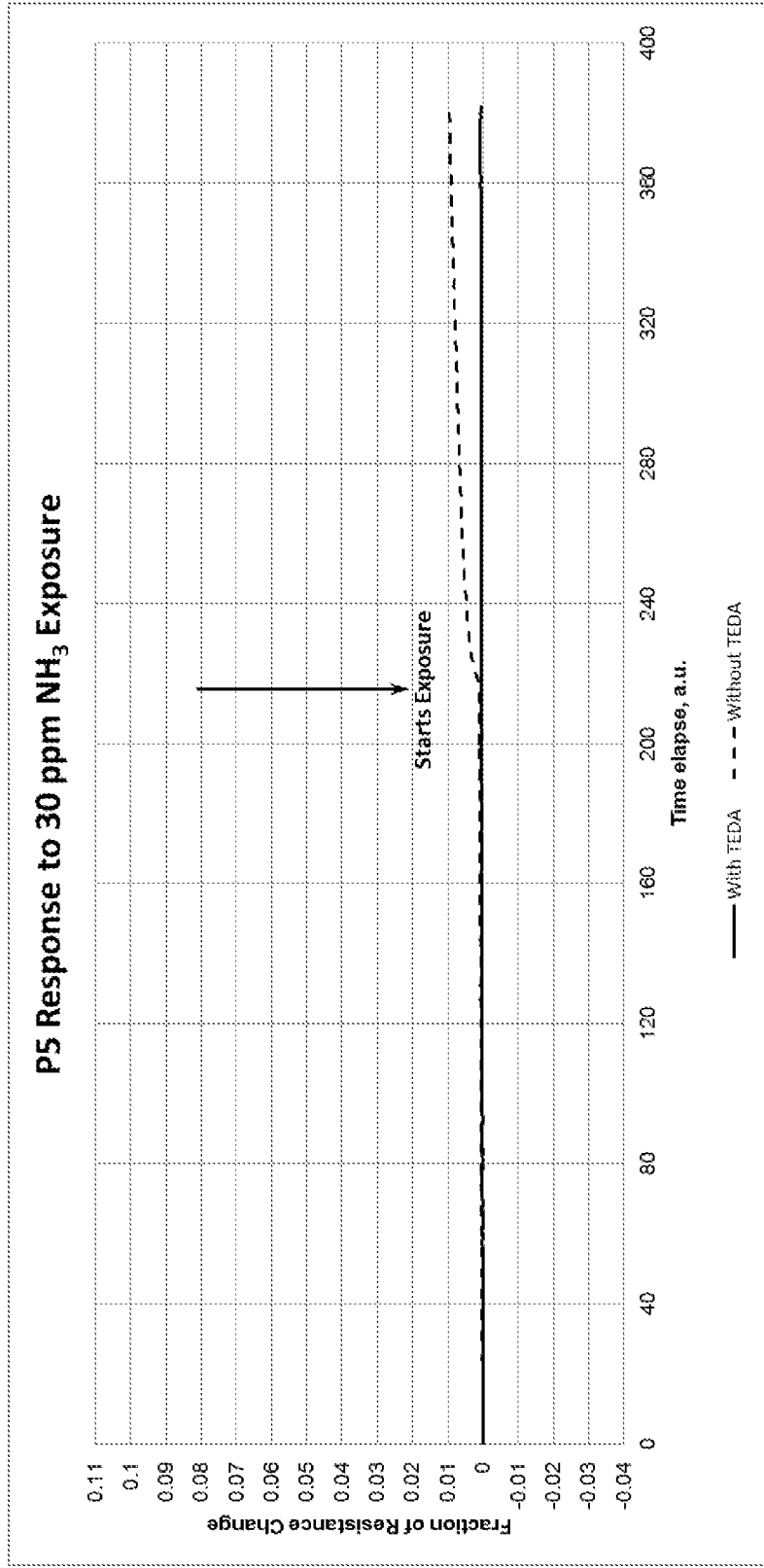
Figure 15A:
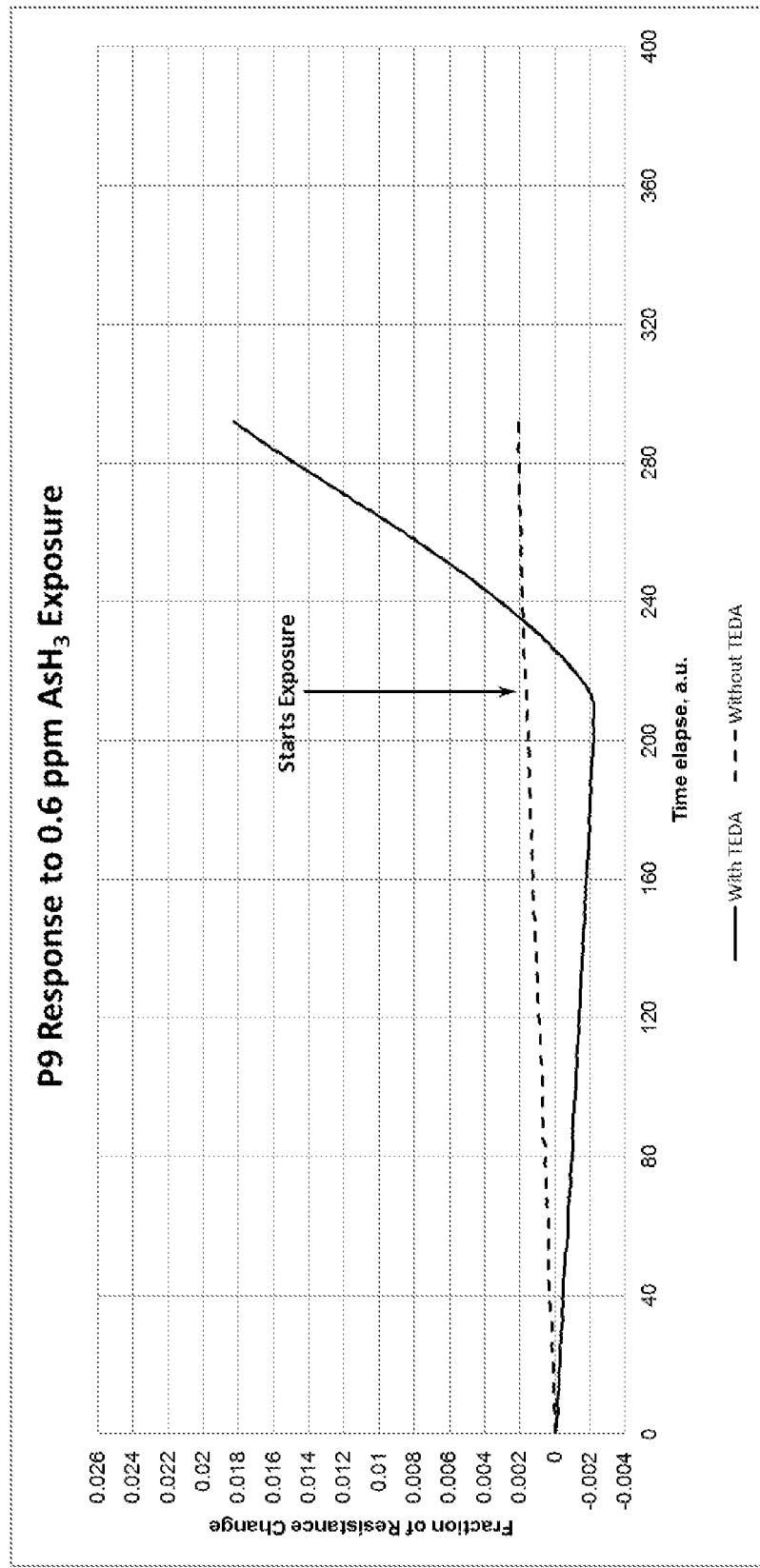
FIG. 15 presents an illustrative example of a display of the output data of the system of FIG. 5, incorporating the multi-type sensor arrays of FIG. 10, upon exposure to arsine ($AsH_3$), according to one exemplary embodiment of the present invention.
Figure 15B:
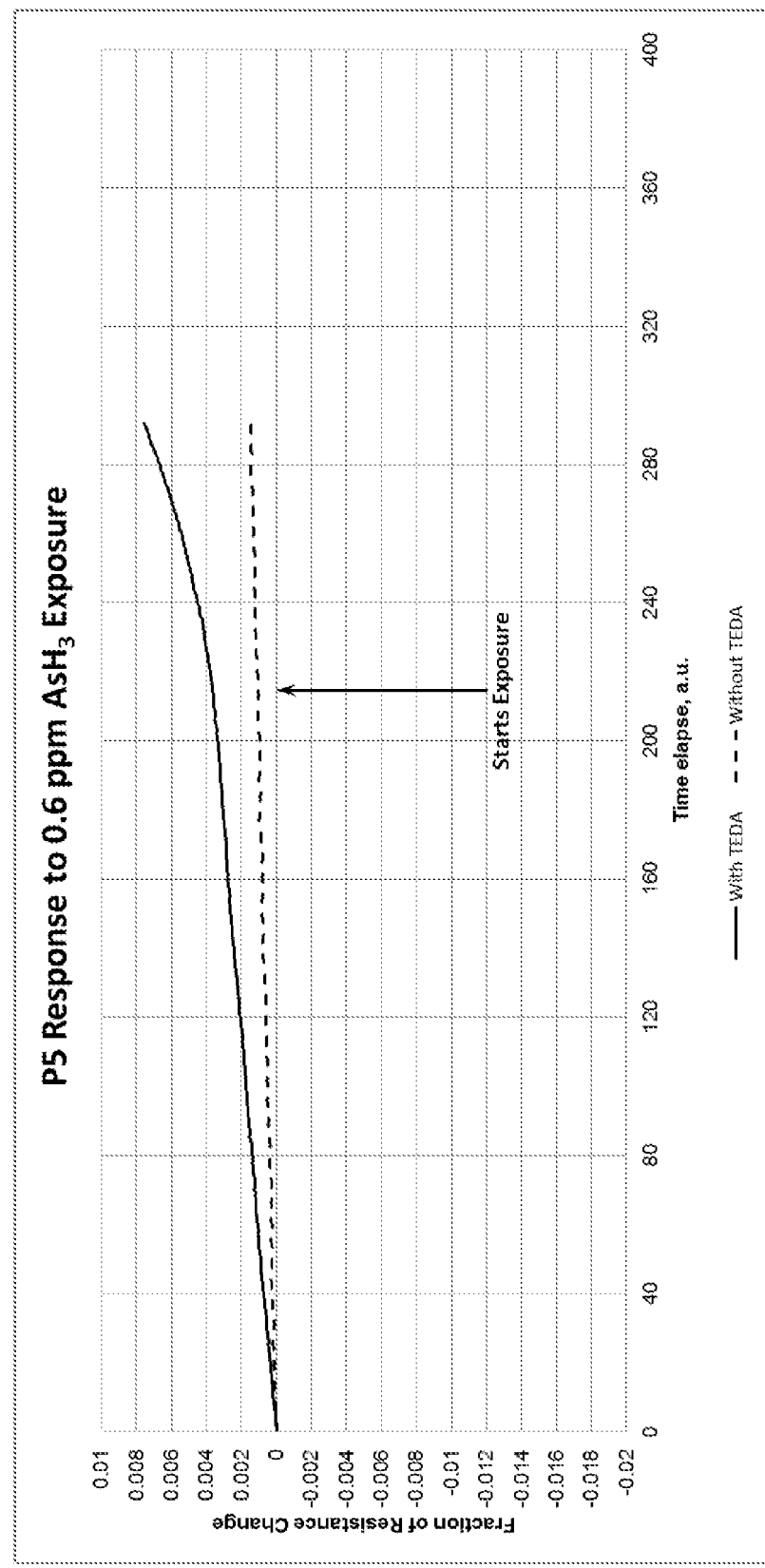
Figure 16A:
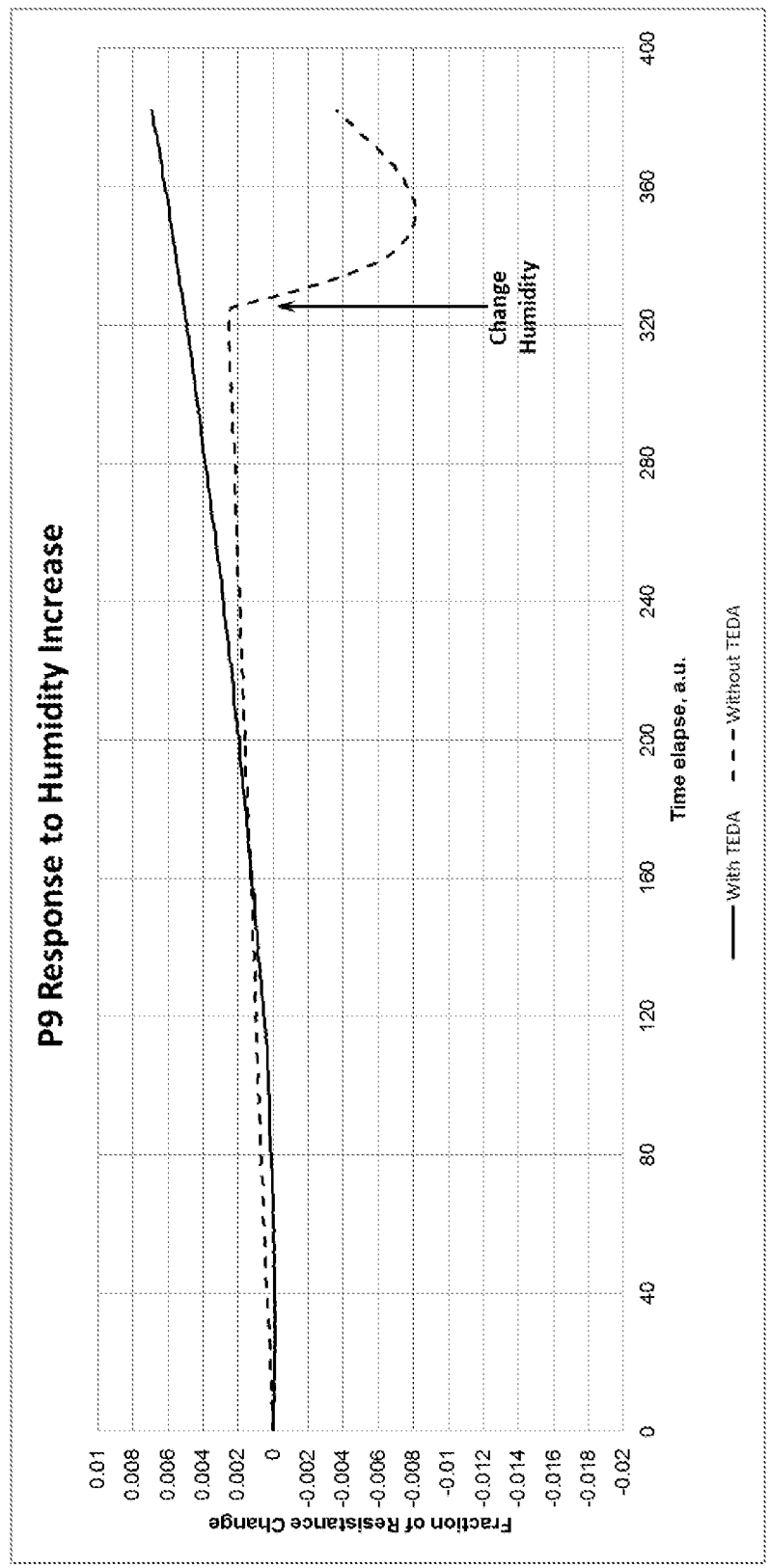
FIG. 16 presents an illustrative example of a display of the output data of the system of FIG. 5, incorporating the multi-type sensor arrays of FIG. 10, upon exposure to increased humidity ($H_2O$), according to one exemplary embodiment of the present invention.
Figure 16B:
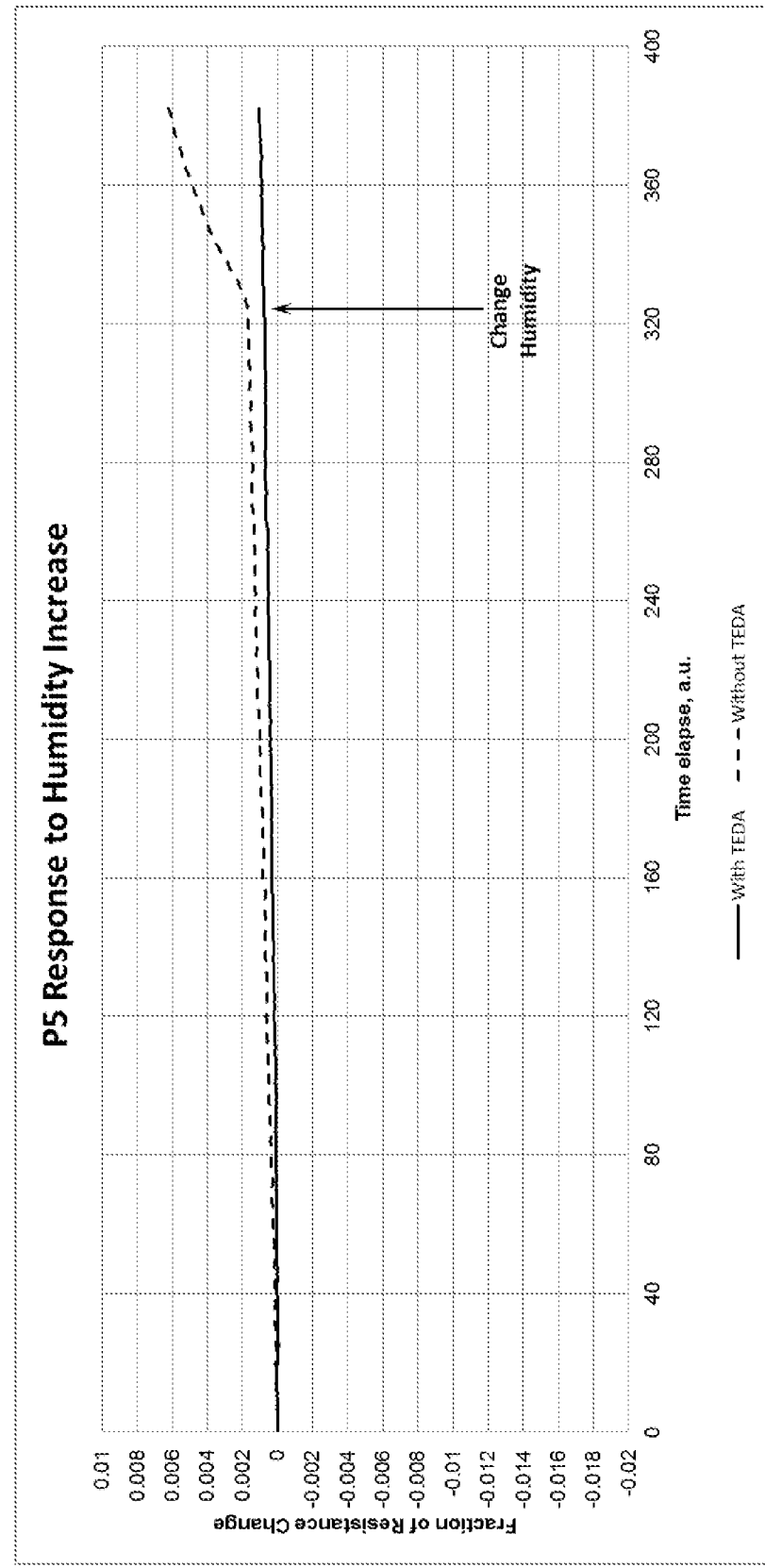
Figure 17A:
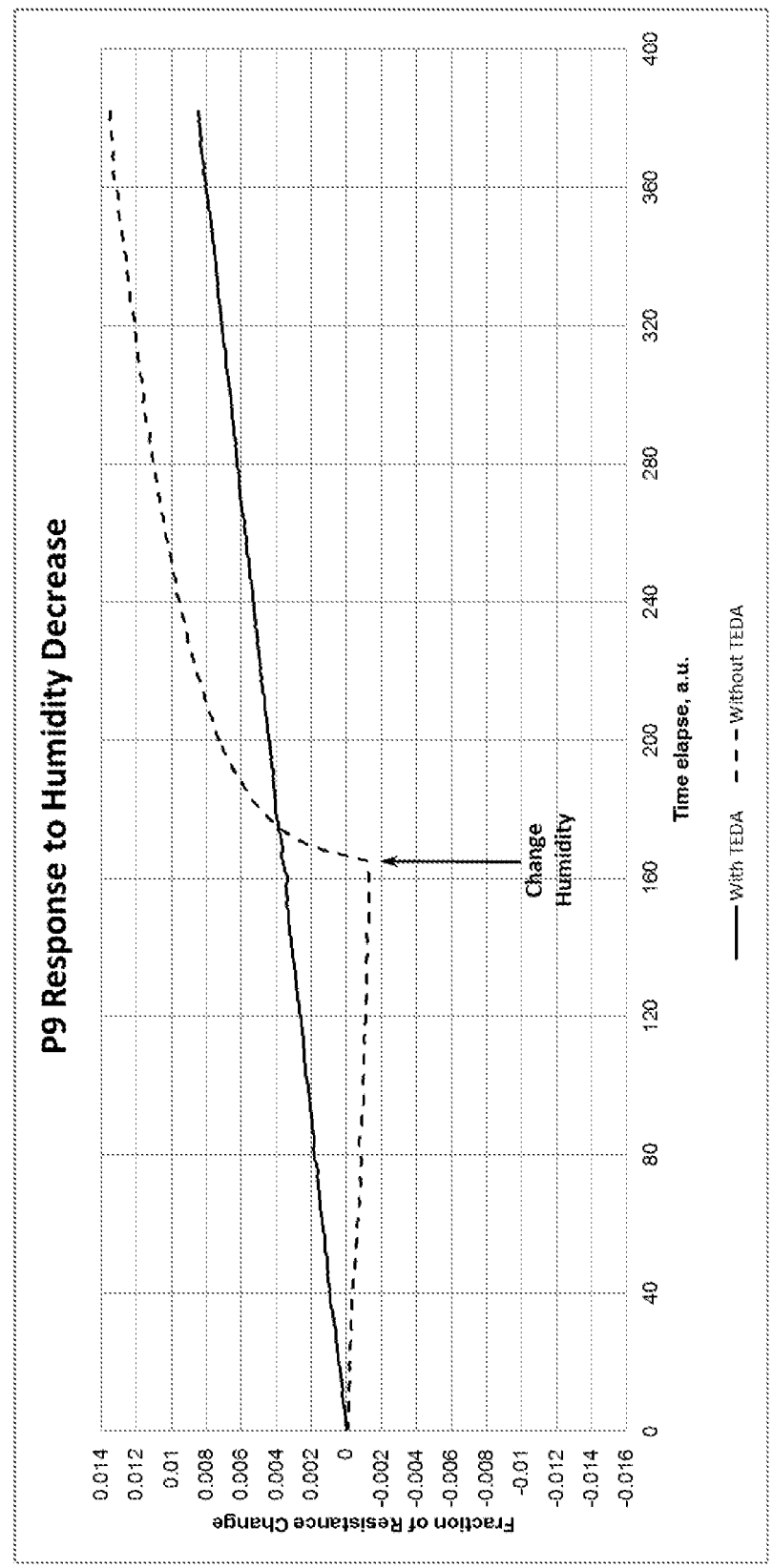
FIG. 17 presents an illustrative example of a display of the output data of the system of FIG. 5, incorporating the multi-type sensor arrays of FIG. 10, upon exposure to decreased humidity ($H_2O$), according to one exemplary embodiment of the present invention.
Figure 17B:
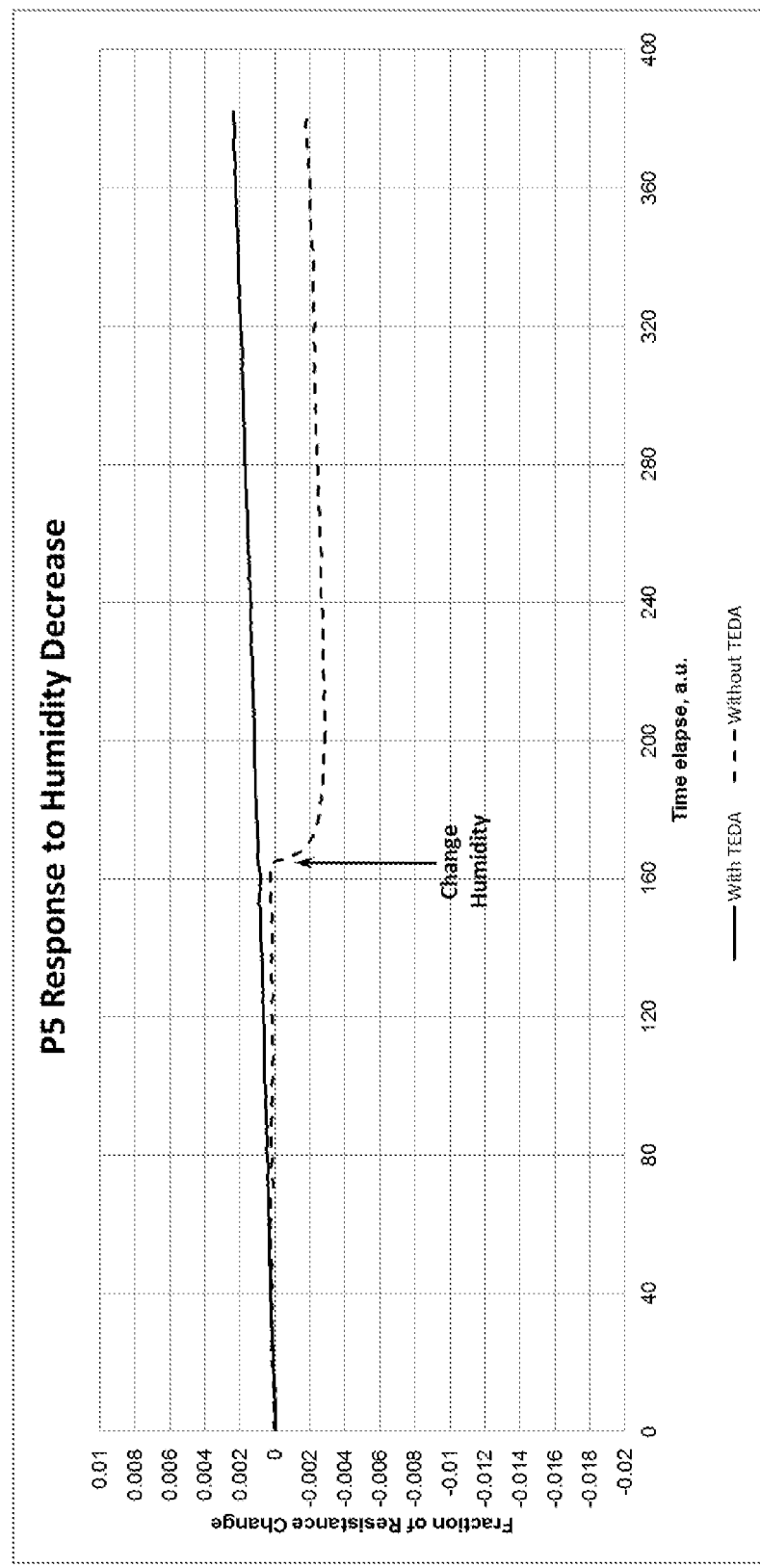

Adhering to the exemplary application wherein CK is the detection target agent of a CNT technology-based sensor, the additive 222 may be TEDA. A significant limitation in the utility and application of CNT sensor technology is limited sensitivity, or the ability of CNTs to detect certain agents or concentration levels of agents of interest. For example, carbon nanotube-based sensor systems do not have the capacity to detect low, yet dangerous concentrations of cyanogen chloride (CK), a key agent of interest in the field of chemical warfare detection. It is known in the field of air purification that the removal of CK from an ambient environmental sample may be accomplished by impregnating activated carbons with an additive, such as triethylenediamine (TEDA). In this application, TEDA chemically reacts with CK, resulting in cyanic acid (HOCN), subsequently decomposing to carbon dioxide ($CO_2$) and ammonia ($NH_3$), accompanied by a series of complex side reactions (not involving TEDA) to form several persistent compounds. When these reaction products are deposited over the surface of certain carbon nanotube-based sensors the electrical properties of the sensors are altered. Therefore, by introducing TEDA to an environmental sample, the presence of CK in the sample may be indicated by the response of the detection system to the reactants.

FIG. 6 presents a detail view of a sensor A 240 of the additive-enhanced detection system 200, according to one embodiment of the present invention. In this exemplary embodiment, sensor A 240 may be designed to measure electrical resistance, and may comprise a pair of gold (Au) electrodes 260/262 physically and electrically separated by a non-conductive gap 264 that may be filled by a carbon nanotube technology coating 266. In one embodiment, the coating 266 may comprise commercially-available polyaminobenzene sulfonic acid functionalized single wall carbon nanotubes, that may be selected for their capability to detect the presence of products of the chemical reaction of TEDA with CK. The electrodes 260/262 may be electrically connected to an instrumentation package 250 by means of signal wires 268/272 that may be in electrical communication with the electrodes 260/262 by means of electrical connections 270/274.

In one exemplary embodiment of the invention, Sensor B 246 may be identical to sensor A 240.

FIG. 7A presents a cross-sectional detail view of an additive reservoir 220 of the additive-enhanced detection system 200, according to one embodiment of the present invention. In this exemplary embodiment, an additive reservoir 220 may comprise a reservoir 280 containing an additive 222. The additive reservoir 220 may further comprise permeable tubing 286 designed to enable the additive 222 to permeate into an environment sample. The additive reservoir 220 may be incorporated into the additive-enhanced detection system 200 by means of transport tubing 284/288.

FIG. 7B presents a cross-sectional detail view of an additive reservoir 320 defining an alternative embodiment of an additive reservoir that may be used in the additive-enhanced detection system 200. In this exemplary embodiment, an additive reservoir 320 may comprise a reservoir 380 containing an additive 322. The additive reservoir 320 may further comprise permeable tubing 386 designed to enable the additive 322 to permeate into an environment sample. The additive reservoir 320 may be incorporated into the additive-enhanced detection system 200 by means of transport tubing 384/388. In this alternative embodiment, the reservoir 380 may define a headspace 390 for additive 322 in vapor form.

Continuing with the example of the detection of CK in a CNT technology-based system, the reaction necessary to produce detectable reactants is dependent upon the presence of water vapor. Reference: *Role of TEDA as an Activated Carbon Impregnant for the Removal of Cyanogen Chloride from Air Streams: Synergistic Effect with Cu(II)*; John J. Hahle, et al.; J. Phys. Chem. C; Vol. 114; 2010; pp. 20083-20090. Further, it is desirable to eliminate the effect of variations in relative humidity on the behavior of the sensors. Therefore, one preferred embodiment of the invention may incorporate a water vapor additive reservoir 218, as shown in FIG. 5. The water vapor additive reservoir 218 may be placed into the flow path 212 upstream of both Path A and Path B. Alternatively, the water vapor additive reservoir 218 may be placed within Path A upstream of sensor array A 238. The water vapor additive reservoir 218 may be designed to maintain a minimum and stable level of relative humidity in the environmental sample (>3% relative humidity) and/or a constant or controlled relative humidity level. The embodiment of the water vapor additive buffer may be the same as or different from that of the additive reservoirs 220 illustrated in FIG. 7. In this exemplary embodiment, the additive 219 may be water and/or water vapor, and the water and/or water vapor may function as a reactant and/or an environmental control.

FIG. 8 presents a flowchart showing the steps of an additive-enhanced method for detecting chemical and/or biological agents employing the additive-enhanced detection system 200 of FIG. 5, according to one embodiment of the present invention.

Step 1: Initiate the simultaneous measurement and monitoring of a discriminating electrical, mechanical, chemical, electrochemical and/or electromechanical property of sensor array A and sensor array B. Measurement of the discriminating electrical, mechanical, chemical, electrochemical and/or electromechanical property may continue throughout the detection process.

Step 2: Initiate flow of an ambient environmental sample through the flow path of the additive-enhanced detector system. The flow may be continuous throughout the detection process.

Step 3: Enhance and/or dampen the moisture content deficiency and/or fluctuation of the ambient environmental sample.

Step 4: Introduce an additive (reactant, selective absorber, and/or catalyst) into the flow path of the ambient environment sample upstream of sensor array A. The additive may be selected for its capacity to react with, or cause a reaction with the detection target chemical and/or biological agent.

Step 5: Simultaneously expose sensor array A to the environmental sample with the additive, and sensor array B to the environmental sample without the additive.

Step 6A: Observe a divergence in the monitored electrical, mechanical, chemical, electrochemical and/or electromechanical property between sensor array A and sensor array B, indicating the presence of a detection target agent; or Step 6B: Observe an absence of divergence in the monitored electrical, mechanical, chemical, electrochemical and/or electromechanical property between sensor array A and sensor array B, indicating the absence of a detection target agent.

FIG. 9 presents an illustrative example of a display of the output data of the additive-enhanced detection method of FIG. 8, showing a divergence in the monitored electrical property between sensor array A 238 and sensor array B 244 in the presence of a detection target agent.

FIG. 10 presents detail schematic views of multi-type sensor arrays that may be used with the additive-enhanced detection system 200 of FIG. 5, according to another embodiment of the present invention. In this embodiment, sensor array A 238 may be populated with a plurality of sensor types, specifically in this exemplary embodiment, sensor type I 290 and sensor type II 292. Similarly, sensor array B 244 may be populated with an identical set of type I sensors 290 and type II sensors 292. Sensor array A 238 is illustrated in FIG. 10 A; sensor array B 244 is illustrated in FIG. 10B. The principal advantage of a multi-type sensor array is enhanced specificity, or the capability to distinguish the agent that is detected. A particular sensor may respond to a variety of chemical and/or biological agents. Adhering to the exemplar of CNT sensors, there exist a plurality of chemical or biological agents that may alter the electrical properties of a CNT sensor, thereby providing an alert as to the presence of a chemical or biological agent. Some of these chemical/biological agents may alter the electrical properties of the CNT sensor in the same direction, magnitude and/or rate as in the CK/TEDA case. Therefore, it is possible to receive a false alert wherein the system may indicate the presence of CK when, in fact, CK is not present.

In one exemplary embodiment, sensor type I 290 may comprise commercially-available amide-functionalized carbon nanotubes, and sensor type II 292 may comprise commercially-available octadecylamine-functionalized carbon nanotubes. In the preferred embodiment of the multi-sensor type additive-enhanced detection system used to develop the exemplary data presented in this specification, the type I sensors 290 and type II sensors 292 were procured from Sigma-Aldrich®. This embodiment may be designed and configured to detect and differentiate the presence of several agents of concern in the field of chemical warfare detection, including hydrogen cyanide (AC), cyanogen chloride (CK), chloride gas ($Cl_2$), ammonia gas ($NH_3$), arsine ($AsH_3$). Further, this embodiment may be designed and configured to detect and differentiate changes in relative humidity of the sample.

A matrix of response data for various environmental conditions is provided in Table I, below. The table identifies the direction of the change in resistance of sensor type I 290 and sensor type II 292 in the presence of the noted agents, with and without the presence of TEDA. The output data employed to build Table I is presented in FIGS. 11 through 17. The data from sensor type I 290 and sensor type II 292 are presented in Figure views A and B, respectively.

TABLE I

Change In Resistance of Type I And Type II Sensors In The Presence Of Selected Chemical Agents - With And Without TEDA Additive

| AGENT | SENSOR TYPE I | | SENSOR TYPE II | |
|---|---|---|---|---|
| | WITH TEDA | W/OUT TEDA | WITH TEDA | W/OUT TEDA |
| None (ambient air) | o | o | o | o |
| Hydrogen Cyanide (AC) | + | o | o | o |
| Cyanogen Chloride (CK) | − | o | − | o |
| Chloride Gas ($Cl_2$) | o | − | o | − |
| Ammonia Gas ($NH_3$) | o | + | o | + |
| Arsine ($AsH_3$) | + | o | + | o |
| Increased Humidity ($H_2O$) | o | − | o | + |
| Decreased humidity ($H_2O$) | o | + | o | − |

+ Indicates increase in signal/resistance
− Indicates decrease in signal/resistance
o Indicates no significant change in signal/resistance As may be seen in Table I, neither sensor type I 290 nor sensor type II 292 will produce a change in signal (resistance) in ambient air. By monitoring the change in resistance of sensor type I 290 and sensor type II 292, in both sensor array A 238 (with TEDA additive) and sensor array B 244 (without TEDA additive), and comparing the monitored responses to the predetermined response predictions of Table I, the additive-enhanced detection system 200 may differentiate between the presence of CK, $Cl_2$, $NH_3$, $AsH_3$, and/or the increase or decrease in humidity.

The simple model represented in Table I may be expanded to monitor and analyze not only the positive/negative direction of the change in resistance, but also the magnitude and rate of the change. The measured response of the sensors may be analyzed to obtain additional information, such as the concentration of agents present in the sampled environment.

Figure 18A:
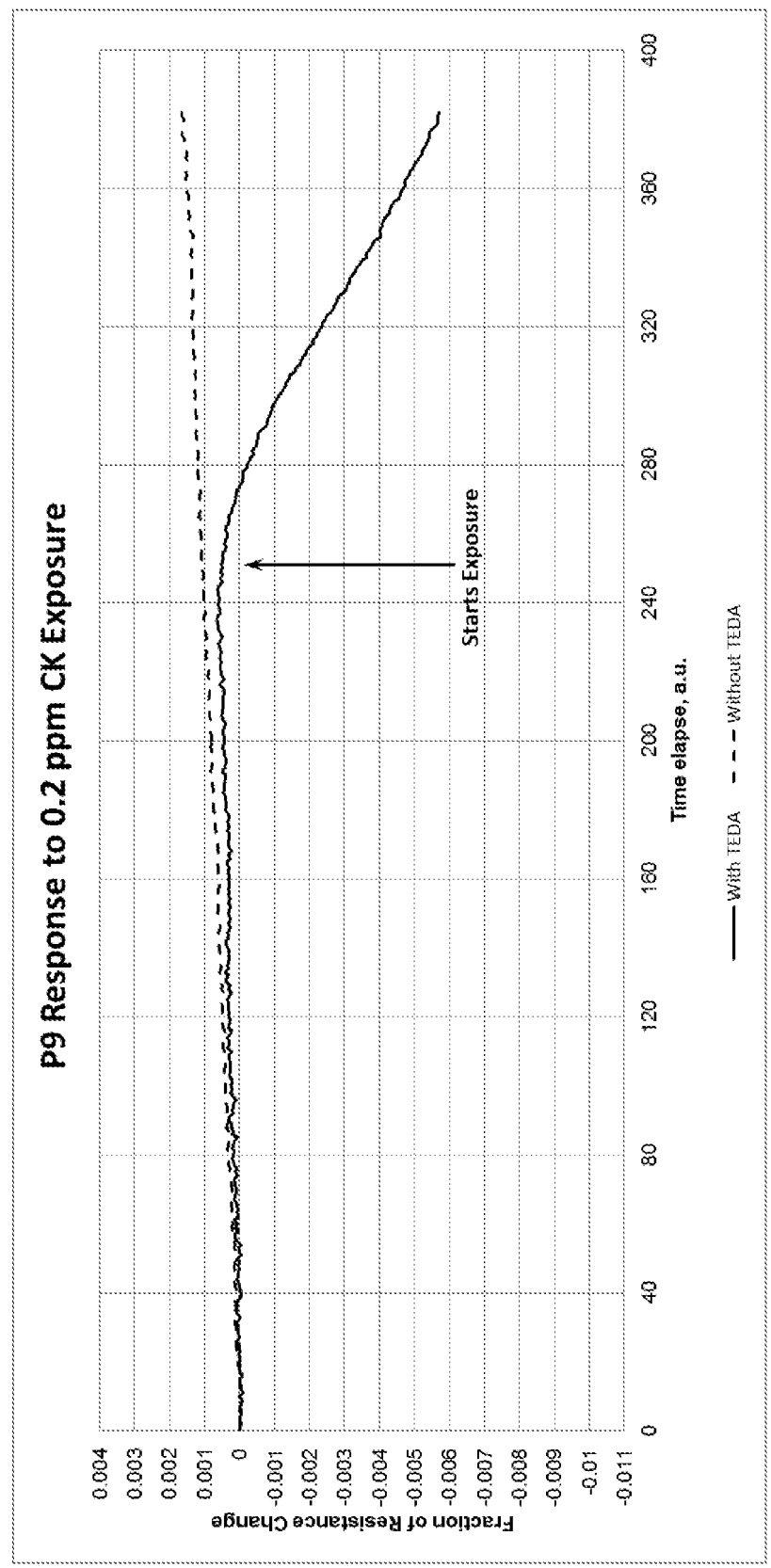
FIG. 18 presents an illustrative example of a display of the output data of the system of FIG. 5, incorporating the multi-type sensor arrays of FIG. 10, upon exposure to a very low concentration (0.2 ppm) of cyanogen chloride (CK), according to one exemplary embodiment of the present invention.
Figure 18B:
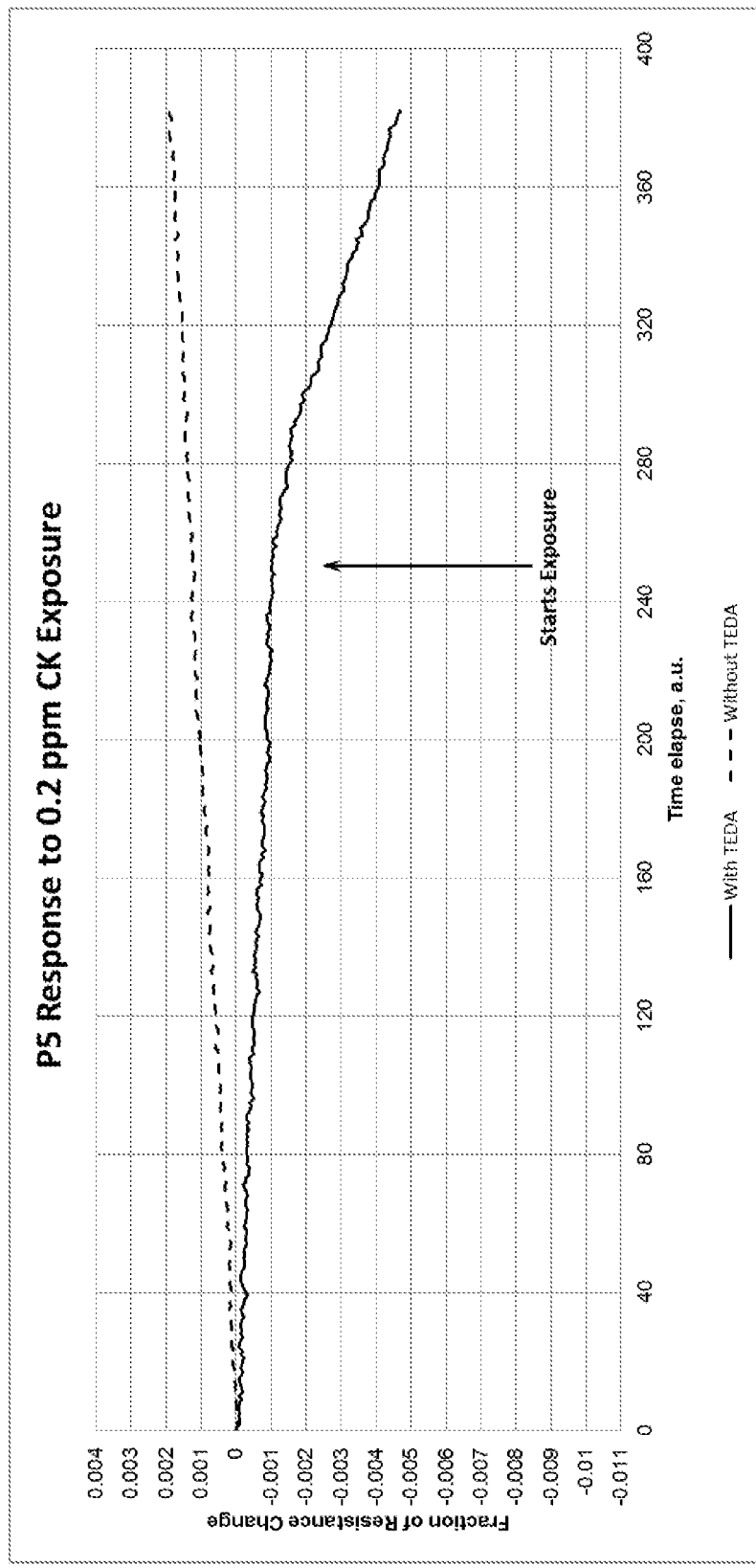

FIG. 18 presents data demonstrating the capacity of the additive-enhanced detection system to detect CK at a concentration level as low as 0.2 ppm.

In alternative embodiments, the system may comprise more than two flow paths. Each of the flow paths may incorporate identical sensors or sensor arrays or, alternatively, each flow path may incorporate a sensor or sensor array that may be selected to provide system selectivity and/or sensitivity with respect to one or more particular chemical and/or biological agent. Further, each flow path may incorporate one or more additive reservoirs and additives that may similarly be selected to provide system selectivity and/or sensitivity with respect to one or more particular chemical and/or biological agent. A particular embodiment of an additive-enhanced detection system may or may not have a control flow path, a control flow path being defined as a flow path in which no additive may be introduced.

As will be apparent to one with skill in the related art, the system and method of the present invention may be used in combination with other, conventional detection devices and methods in order to provide an additional detection dimension, such as enhancing the specificity (the ability to identify a detected agent) or sensitivity (the ability to detect small concentrations of an agent) of the conventional device/method, or to enable the conventional device/method to detect and identify a larger set of agents.

The elements of an additive-enhanced detection system may be modified, interchanged, separated or combined, or additional elements added without departing from the spirit of the invention. The invention may be practiced in alternative embodiments other than those illustrated in the Figures. Such modifications, combinations, additions and alternatives are within the contemplation of the present invention. The individual steps of the disclosed methods of using an additive-enhanced detection system may be modified, interchanged, separated or combined, or additional steps added without departing from the spirit of the invention. The exemplary embodiments and methods disclosed are not intended to limit the scope of this invention. Accordingly, the scope of the invention should be determined not by the embodiments illustrated, but by their legal equivalents, and shall be as broad as the claims will allow.

What is claimed is:

1. A system for detecting the presence of chemical and/or biological agents, comprising:
    a first flow path in communication with an ambient air environment;
    a second flow path in communication with said ambient air environment;

a first sensor array connected to said first flow path so as to sense gaseous contents of said first flow path; said first sensor array comprising a first sensor type and a second sensor type, each of which configured to sense a chemical or biological agent;

a second sensor array connected to said second flow path so as to sense gaseous contents of said second flow path; said second sensor array comprising said first sensor type and said second sensor type;

a first additive reservoir containing a first additive selected from a reactant, selective absorber, and a catalyst; said first additive reservoir being connected to and in communication with said first flow path, upstream of said first sensor array; and, an instrumentation package electrically connected to said first sensor array and said second sensor array; said instrumentation package simultaneously measuring with said first sensor type and said second sensor type from both of said first sensor array and said second sensor array; and said instrumentation package monitoring for a divergence between sensor readings from said first sensor type and sensor readings from said second sensor type;

wherein said first sensor type includes amide-functionalized carbon nanotubes and said second sensor type includes octadecylamine-functionalized carbon nanotubes.

2. The system of claim 1, wherein said first sensor array and said second sensor array each further include a third sensor type comprising polyaminobenzene sulfonic acid functionalized carbon nanotubes.

3. The system of claim 1, further comprising a pump in communication with said first flow path and said second flow path, so as to move ambient air through said first flow path and said second flow path.

4. The system of claim 1, wherein said instrumentation package further comprises a microprocessor, machine-readable memory, and an output communication system.

5. The system of claim 1, wherein said first additive is triethylenediamine (TEDA), diethylenediamine, porphyrin, tris(ethylenediamine)nickel (II) chloride, hydrogen peroxide, water/water vapor, and/or ozone.

6. The system of claim 5, wherein said instrumentation package is configured to detect hydrogen cyanide (AC), cyanogen chloride (CK), chloride gas ($Cl_2$), ammonia gas ($NH_3$), and arsine ($AsH_3$).

7. The system of claim 5, wherein said instrumentation package measures electrical resistance for each of said first sensor type and of said second sensor type.

8. A system for detecting the presence of chemical and/or biological agents, comprising:
   a first flow path in communication with an ambient air environment;
   a second flow path in communication with said ambient air environment;
   a first sensor array connected to said first flow path so as to sense gaseous contents of said first flow path;
   a second sensor array connected to said second flow path so as to sense gaseous contents of said second flow path;
   a first additive reservoir containing a first additive selected from a reactant, selective absorber, and a catalyst; said first additive reservoir being connected to and in communication with said first flow path, upstream of said first sensor array; and,
   an instrumentation package electrically connected to said first sensor array and said second sensor array;
   wherein said first sensor array contains a first plurality of sensors that measure the same chemical or biological agents of a second plurality of sensors in said second sensor array; wherein said instrumentation package simultaneously measures with said first plurality of sensors and said second plurality of sensors from both of said first sensor array and said second sensor array; and,
   wherein said first plurality of sensors and said second plurality of sensors include a first sensor type of amide-functionalized carbon nanotubes and a second sensor type of octadecylamine-functionalized carbon nanotubes.

9. The system of claim 8, wherein said first additive is triethylenediamine (TEDA), diethylenediamine, porphyrin, tris(ethylenediamine)nickel (II) chloride, hydrogen peroxide, water/water vapor, and/or ozone.

10. The system of claim 8, wherein said first sensor array and said second sensor array each further include a third sensor type comprising polyaminobenzene sulfonic acid functionalized carbon nanotubes.

11. The system of claim 8, wherein said first additive is in solid, liquid, or vapor form.

12. The system of claim 8, further comprising a second additive reservoir containing a second additive selected from a reactant, selective absorber, and a catalyst; said second additive reservoir being connected to and in communication with said first flow path and said second flow path.

* * * * *